(12) United States Patent
Hirao et al.

(10) Patent No.: US 7,960,543 B2
(45) Date of Patent: *Jun. 14, 2011

(54) NUCLEOSIDE OR NUCLEOTIDE DERIVATIVE AND USE THEREOF

(75) Inventors: Ichiro Hirao, Yokohama (JP); Shigeyuki Yokoyama, Yokohama (JP)

(73) Assignee: RIKEN, Saitama (JP)

( * ) Notice: Subject to any disclaimer, the term of this patent is extended or adjusted under 35 U.S.C. 154(b) by 436 days.

This patent is subject to a terminal disclaimer.

(21) Appl. No.: 11/667,146

(22) PCT Filed: Nov. 8, 2005

(86) PCT No.: PCT/JP2005/020435
§ 371 (c)(1),
(2), (4) Date: Jun. 11, 2008

(87) PCT Pub. No.: WO2006/049297
PCT Pub. Date: May 11, 2006

(65) Prior Publication Data
US 2009/0275017 A1 Nov. 5, 2009

(30) Foreign Application Priority Data
Nov. 8, 2004 (JP) ................. 2004-324271

(51) Int. Cl.
| C07H 21/00 | (2006.01) |
| C07H 21/02 | (2006.01) |
| C07H 19/04 | (2006.01) |
| C12Q 1/68  | (2006.01) |
| C12P 19/34 | (2006.01) |
| C07G 11/00 | (2006.01) |

(52) U.S. Cl. ...... 536/26.6; 536/4.1; 536/23.1; 536/24.3; 435/6; 435/91.1

(58) Field of Classification Search .................. 536/4.1, 536/23.1, 24.3, 26.6; 435/6, 91.1
See application file for complete search history.

(56) References Cited

U.S. PATENT DOCUMENTS

| 5,925,517 A | 7/1999 | Tyagi et al. |
| 6,103,476 A | 8/2000 | Tyagi et al. |

(Continued)

FOREIGN PATENT DOCUMENTS

JP    9-504950 A    5/1997

(Continued)

OTHER PUBLICATIONS

Moriyama, Kei et al., "Site-specific biotinylation of RNA molecules by transcription using unnatural base pairs," *Nucleic Acids Research*, 2005, vol. 33, No. 15, e129.

(Continued)

*Primary Examiner* — Jezia Riley
(74) *Attorney, Agent, or Firm* — Birch, Stewart, Kolasch & Birch, LLP

(57) ABSTRACT

The object of the present invention is to provide a nucleoside or nucleotide having a 5-substituted-2-oxo(1H)pyridin-3-yl group as a base, as well as a method using the same.

In one embodiment, the nucleoside or nucleotide of the present invention has a fluorescent dye selected from the group consisting of 5-FAM, 6-FAM, 5-TAMRA, 6-TAMRA, DANSYL, 5-HEX, 6-HEX, 5-TET, 6-TET, 5-ROX and 6-ROX or a quencher dye selected from the group consisting of DABCYL, BHQ1 and BHQ2, which is attached either directly or through a linker to the 5-position of the above base.

15 Claims, 12 Drawing Sheets

U.S. PATENT DOCUMENTS 6,664,079 B2 * 12/2003 Ju et al. .................. 435/91.1
7,745,417 B2 * 6/2010 Hirao et al. ................ 514/44 R

FOREIGN PATENT DOCUMENTS

WO    WO-2004/007713 A1    1/2004

OTHER PUBLICATIONS

Kawai, Rie et al., "Site-specific fluorescent labeling of RNA molecules by specific transcription using unnatural base pairs," *J. Am. Chem. Soc.*, 2005, vol. 127, pp. 17286-17295.

Hirao, Ichiro, "Placing extra components into RNA by specific transcription using unnatural base pair systems," *BioTechniques*, Jun. 2006, vol. 40, No. 6, pp. 711-717.

Boguszewska-Chachulska, et al., "Direct fluorometric measurement of hepatitis C virus helicase activity," FEBS Lett., 567, pp. 253-258 (2004).

Chehab, et al., "Detection of specific DNA sequences by fluorescence amplification: a color complementation assay," Proc.Natl.Acad.Sci. USA, 86, pp. 9178-9182 (1989).

Clore, et al., "Improving the accuracy of NMR structures of RNA by means of conformational database potentials of mean force as assessed by complete dipolar coupling cross-validation," J.Am. Chem.Soc., 125, pp. 1518-1525 (2003).

Dragon, et al., "DNA-binding domain of GCN4 induces bending of both the ATF/CREB and AP-1 binding sites of DNA," Nucleic Acids Res., 32, pp. 5192-5197 (2004).

Ellington, et al., "In vitro selection of RNA molecules that bind specific ligands," Nature, 346, pp. 818-822 (1990).

Endo, et al., "Unnatural base pairs mediate the site-specific incorporation of an unnatural hydrophobic component into RNA transcripts," Bioorg.Med.Chem.Lett., 14, pp. 2593-2596 (2004).

Fang, et al., "Molecular aptamer for real-time oncoprotein platelet-derived growth factor monitoring by fluorescence anistropy," Anal. Chem., 73, pp. 5752-5757 (2001).

Frauendorf, et al., "Detection of small organic analytes by fluorescing molecular switches," Bioorg.Med.Chem., 9, pp. 2521-2524 (2001).

Fujiwara, et al., "Synthesis of 6-(2-Thienyl)purine Nucleoside Derivatives That Form Unnatural Base Pairs with Pyridin-2-one Nucleosides," Bioorg.Med.Chem.Lett., 11, pp. 2221-2223 (2001).

Gibson, et al., "A novel method for real time quantitative RT-PCR," Genome Res., 6, pp. 995-1001 (1996).

Golden, et al., "Diagnostic potential of PhotoSELEX-evolved ssDNA aptamers," J.Biotechnol., 81, pp. 167-178 (2000).

Hirao, et al., "An unnatural base pair for incorporating amino acid analogs into proteins," Nat.Biotechnol., 20, pp. 177-182 (2002).

Hirao, et al., "RNA Aptamers That Bind to and Inhibit the Ribosome-inactivating Protein, Pepocin," J.Biol.Chem., 275, pp. 4943-4948 (2000).

Ishikawa, et al., "Synthesis of 3-(2-deoxy-β-D-ribofuranosyl)pyridine-2-one and 2-amino-6(N,N-dimethylamino)-9-(2-deoxy-β-D-ribofuranosyl)purine derivatives for an unnatural base pair," Tetrahedron Lett., 41, pp. 3931-3934 (2000).

Jenison, et al., "High-resolution molecular discrimination by RNA," Science, 263, pp. 1425-1429 (1994).

Jensen, et al., "Using in vitro selection to direct the covalent attachment of human immunodeficiency virus type 1 Rev protein to high-affinity RNA ligands," Proc.Natl.Acad.Sci.USA, 92 pp. 12220-12224 (1995).

Jhaveri, et al., "In vitro selection of signaling aptamers," Nat. Biotechnol., 18, pp. 1293-1297 (2000).

Jucker, et al., "Role of a heterogeneous free state in the formation of a specific RNA-theophylline complex," Biochemistry, 42, pp. 2560-2567 (2003).

Kimoto, et al., "Anti-(Raf-1) RNA aptamers that inhibit Ras-induced Raf-1 activation," Eur.J.Biochem., 269, pp. 697-704 (2002).

Kimoto, et al., "Site-specific incorporation of a photo-crosslinking component into RNA by T7 transcription mediated by unnatural base pairs," Chem.Biol., 11, pp. 47-55 (2004).

Latham, et al., "The application of a modified nucleotide in aptamer selection: novel thrombin aptamers containing 5-(1-pentynyl)-2'-deoxyuridine," Nucleic Acids Res., 22, pp. 2817-2822 (1994).

Logsdon, et al., "Selective 5' modification of T7 RNA polymerase transcripts," Anal.Biochem., 205, pp. 36-41 (1992).

Matulic-Adamic, et al., "Synthesis of 3-(β-D-Ribofuranosyl)-2-Fluoropyridine and 3-(β-3-D-Ribofuranosyl)-Pyridin-2-one," Tetrahedron Lett., 38, pp. 203-206 (1997).

Meisenheimer, et al., "Photocross-Linking of Nucleic Acids to Associated Proteins," Crit.Rev.Biochem.Mol.Biol., 32, pp. 101-140 (1997).

Misra, et al., "Synthesis and fluorescence studies of multiple labeled oligonucleotides containing dansyl fluorophore covalently attached at 2'-terminus of cytidine via carbamate linkage," Bioconjugate Chem., 15, pp. 638-646 (2004).

Moriyama, et al., "Site-specific biotinylation of RNA molecules by transcription using unnatural base pairs," Nucleic Acids Res., 33, e129 (2005).

Ohtsuki, et al., "Unnatural base pairs for specific transcription," Proc.Natl.Acad.Sci.USA, 98, pp. 4922-4925 (2001).

Patel, et al., "Structure, recognition and discrimination in RNA aptamer complexes with cofactors, amino acids, drugs and aminoglycoside antibiotics," Reviews in Molecular Biotechnology, 74, pp. 39-60 (2000).

Piccirilli, et al., "A C-nucleotide base pair: methylpseudouridine-directed incorporation of formycin triphosphate into RNA catalyzed by T7 RNA polymerase," Biochemistry, 30, pp. 10350-10356 (1991).

Piccirilli, et al., "Enzymatic incorporation of a new base pair into DNA and RNA extends the genetic alphabet," Nature, 343, pp. 33-37 (1990).

Sibille, et al., "Refinement of local and long-range structural order in theophylline-binding RNA using (13)C-(1)H residual dipolar couplings and restrained molecular dynamics," J.Am.Chem.Soc., 123, pp. 12135-12146 (2001).

Stojanovic, et al., "Modular aptameric sensors," J.Am.Chem.Soc., 126, pp. 9266-0270 (2004).

Switzer, et al., "Enzymatic Recognition of the Base Pair between Isocytidine and Isoguanosine," Biochemistry, 32, pp. 10489-10496 (1993).

Tyagi, et al., "Molecular beacons: probes that fluoresce upon hybridization," Nat.Biotechnol., 14, pp. 303-308 (1996).

Watrob, et al, "Two-step FRET as a structural tool," J.Am.Chem. Soc., 125, pp. 7336-7343 (2003).

Wu, et al., "Efforts toward Expansion of the Genetic Alphabet: Optimization of Interbase Hydrophobic Interactions," J.Am.Chem.Soc., 122, pp. 7621-7632 (2000).

Yamamoto, et al., "Molecular beacon aptamer fluorescences in the presence of Tat protein of HIV-1," Genes Cells, 5, pp. 389-396 (2000).

Zimmerman, et al., "A semiconserved residue inhibits complex formation by stabilizing interactions in the free state of a theophylline-binding RNA," Biochemistry, 37, pp. 9186-9192 (1998).

Zimmerman, et al., "Interlocking structural motifs mediate molecular discrimination by a theophylline-binding RNA," Nat.Struct.Biol., 4, pp. 644-649 (1997).

Zimmerman, et al., "Molecular interactions and metal binding in the theophylline-binding core of an RNA aptamer," RNA, 6, pp. 659-667 (2000).

Tor, Y., et al., "Site-Specific Enzymatic Incorporation of an Unnatural Base, $N^6$-(6- Aminohexyl)isoguanosine, into RNA," J. Am. Chem. Soc., vol. 115, pp. 4461-4467 (1993).

Mergny, et al., "Fluorescence entergy transfer as a probe for nucleic acid structures and sequences," Nucleic Acids Res., 22, pp. 920-928 (1994).

Tuschl, et al., "A three-dimensional model for the hammerhead ribozyme based on fluorescence measurements," Science, 266, pp. 785-789 (1994).

Battersby, et al., "Quantititave Analysis of Receptors for Adenosine Nucleotides Obtained via In Vitro Selection from a Library Incorporating a Cationic Nucleotide Analog." J.Am.Chem.Soc., 121, pp. 9781-9789 (1999).

Bernacchi, et al., "Exciton interaction in molecular beacons: a sensitive sensor for short range modifications of the nucleic acid structure," Nucleic Acids Res., 29, p. e62 (2001).

Klostermeier, et al., "RNA conformation and folding studied with fluorescence resonance energy transfer," Methods, 23, pp. 240-254 (2001).

Morales, et al, "Minor Groove Interactions between Polymerase and DNA: More Essential to Replication than Watson-Crick Hydrogen Bonds?," J.Am.Chem.Soc., 121, pp. 2323-2324 (1999).

Tae, et al., "Efforts toward Expansion of the Genetic Alphabet: Replication of RNA with Three Base Pairs," J.Am.Chem.Soc., 123, pp. 7439-7440 (2001).

Walter, N.G., "Structural dynamics of catalytic RNA highlighted by fluorescence resonance energy transfer," Methods, 25, pp. 19-30 (2001).

* cited by examiner a. Absorption spectra of FAM-yTP and TAMR-yTP b. Fluorescence spectra of FAM-yTP and TAMR-yTP

Figure 5a non-template: 5'-ATAATACGACTCACTATAGGG
template: 3'-TATTATGCTGAGTGATATCCCTTAGGGCTCNTCAC ↓ T7 RNA polymerase
1 mM NTPs (N'= A, G, C, U, and modified yTP)
[γ-32P]GTP, 37°C, 3 h 5'pppGGGAAUCCCGAGN'AGUG
+1  +13  +17

| modified yTP | NH₂-yTP | | | FAM-yTP | | | TAMRA-yTP | | |
|---|---|---|---|---|---|---|---|---|---|
| template N | y | s | A | y | s | A | y | s | A |

17-mer(modified) ►
17-mer(native) ►

12-mer ►

| | 1 | 2 | 3 | 4 | 5 | 6 | 7 | 8 | 9 |
|---|---|---|---|---|---|---|---|---|---|
| relative yields (%) | 103 | 49 | 100 | 76 | 26 | 100 | 61 | 21 | 100 |

Figure 5b a
```
5'-ATAATACGACTCACTATAGGG
3'-TATTATGCTGAGTGATATCCCTTAGGGCTCNTCAC
  temp35N-1 (N=v or A)         +1              +13   +17
```
| T7 RNA polymerase
| 1 mM natural NTPs
| 1 mM modified-yTP
| [γ-³²P]GTP
↓ 37°C, 3 h 5'-³²pppGGGAAUCCCGAGN'AGUG b

| Modified-yTP | short PAM-y | | PAM-y | | TAMRA-y | | Dansyl-x-y | | |
|---|---|---|---|---|---|---|---|---|---|
| Template N | v | A | v | A | v | A | v | A | A |
| Relative yields (%) | 72 | 108 | 80 | 96 | 62 | 110 | 48 | 94 | 100 |

17-mer(modified)
17-mer(native)
12-mer 1  2  3  4  5  6  7  8  9

SEQUENCE LISTING

```
<160> NUMBER OF SEQ ID NOS: 8

<210> SEQ ID NO 1
<211> LENGTH: 35
<212> TYPE: DNA
<213> ORGANISM: Artificial sequence
<220> FEATURE:
<223> OTHER INFORMATION: Synthesized template strand for transcription
<220> FEATURE:
<221> NAME/KEY: misc_feature
<222> LOCATION: (5)..(5)
<223> OTHER INFORMATION: n means 2-amino-6-(2-thiazolyl)-purine-9-yl,
      2-amino-6-(2-thienyl)-purine-9-yl or "a"
```

<400> SEQUENCE: 1
cactnctcgg gattccctat agtgagtcgt attat          35

<210> SEQ ID NO 2
<211> LENGTH: 21
<212> TYPE: DNA
<213> ORGANISM: Artificial sequence
<220> FEATURE:
<223> OTHER INFORMATION: Synthesized template strand for transcription

<400> SEQUENCE: 2
ataatacgac tcactatagg g          21

<210> SEQ ID NO 3
<211> LENGTH: 17
<212> TYPE: RNA
<213> ORGANISM: Artificial sequence
<220> FEATURE:
<223> OTHER INFORMATION: Synthesized template strand for transcription
<220> FEATURE:
<221> NAME/KEY: misc_feature
<222> LOCATION: (13)..(13)
<223> OTHER INFORMATION: n means NH2-2-oxo-(1H)-pyridine, FAM-2-oxo-
      (1H)-pyridine or TAMRA-2-oxo-(1H)-pyridine

<400> SEQUENCE: 3
gggaaucccg agnagug          17

<210> SEQ ID NO 4
<211> LENGTH: 98
<212> TYPE: RNA
<213> ORGANISM: Artificial sequence
<220> FEATURE:
<223> OTHER INFORMATION: RNA aptamer

<400> SEQUENCE: 4
gggaguggag gaauucugag gcauaugucg acuccgucuu ccuucaaacc aguauaaau          60 ugguuuuagc auaugccuua gcgacagcaa gcuucugc          98

<210> SEQ ID NO 5
<211> LENGTH: 39
<212> TYPE: DNA
<213> ORGANISM: Artificial sequence
<220> FEATURE:
<223> OTHER INFORMATION: Designed primer for PCR

<400> SEQUENCE: 5
ggtaatacga ctcactatag ggagtggagg aattcatcg          39

<210> SEQ ID NO 6
<211> LENGTH: 29
<212> TYPE: DNA
<213> ORGANISM: Artificial sequence
<220> FEATURE:
<223> OTHER INFORMATION: Designed primer for PCR
<220> FEATURE:
<221> NAME/KEY: misc_feature
<222> LOCATION: (11)..(11)
<223> OTHER INFORMATION: n means 2-amino-6-(2-thiazolyl)-purine-9-yl

<400> SEQUENCE: 6
gcagaagctt nctgtcgcta aggcatatg          29

<210> SEQ ID NO 7
<211> LENGTH: 59
<212> TYPE: DNA

```
<213> ORGANISM: Artificial sequence
<220> FEATURE:
<223> OTHER INFORMATION: Synthesized template strand for transcription
<220> FEATURE:
<221> NAME/KEY: misc_feature
<222> LOCATION: (33)..(33)
<223> OTHER INFORMATION: n means 2-amino-6-(2-thienyl)-purine-9-yl or
      "a"

<400> SEQUENCE: 7
gagcgctgcc aagggcgact ttcgtcgctg gtntcgctcc ctatagtgag tcgtattat          59

<210> SEQ ID NO 8
<211> LENGTH: 41
<212> TYPE: RNA
<213> ORGANISM: Artificial sequence
<220> FEATURE:
<223> OTHER INFORMATION: Synthesized RNA transcript
<220> FEATURE:
<221> NAME/KEY: misc_feature
<222> LOCATION: (9)..(9)
<223> OTHER INFORMATION: n means NH2-2-oxo-(1H)-pyridine, Ph-2-oxo-
      (1H)-pyridine or I-2-oxo-(1H)-pyridine

<400> SEQUENCE: 8
gggagcgana ccagcgacga aagucgcccu uggcagcgcu c                            41
```

NUCLEOSIDE OR NUCLEOTIDE DERIVATIVE AND USE THEREOF

TECHNICAL FIELD

The present invention relates to nucleosides or nucleotides having novel unnatural bases and uses thereof.

BACKGROUND ART

In nucleic acids (DNA, RNA) which are biological macromolecules, enormous amounts of genetic information essential for vital activities are recorded as sequences composed of combinations of only 4 different bases. Such a nucleic acid allows self-replication using itself as a template by the action of DNA polymerases, and further undergoes processes of RNA polymerase-mediated transcription and ribosome-mediated translation to ensure the transmission of genetic information from DNA to DNA, from DNA to RNA, and/or from RNA to protein. These replication and transmission events of genetic information enabled exclusive base-pairings (A:T/U, G:C). In addition, nucleic acids can form a variety of higher-order structures and hence exert various functions. By way of example, it is one of the indications that a large number of novel nucleic acids having aptamer and/or ribozyme functions have been generated by in vitro selection techniques.

However, unlike proteins which are composed of 20 types of amino acids, the chemical and physical diversity of nucleic acids is limited by the fact that there are only 4 different bases (2 base pairs) in natural nucleic acids. For example, functional RNAs (e.g., tRNA, rRNA, mRNA) found in living organisms utilize various modified bases to stabilize their own structures and/or RNA-RNA and RNA-protein interactions. Thus, it will be very advantageous to expand the repertory of new bases (base pairs) in developing novel functional nucleic acids.

With the aim of further expansion of nucleic acid functions, attempts have been made to design nucleosides or nucleotides having unnatural bases. There are two possible approaches for introducing modified bases (or unnatural bases) into nucleic acids: 1) direct introduction by chemical synthesis; and 2) introduction catalyzed by DNA and RNA polymerase enzymes. In the case of 1), there is a need to solve some problems associated with chemical synthesis, such as the stability of amidite units and the presence of protecting groups appropriate for base moieties. If these problems are solved, various unnatural bases can be introduced in a site-selective manner. However, the nucleic acids thus obtained are difficult to be amplified and it is also difficult to synthesize long-chain nucleic acids. In the case of 2), if the enzymes recognize substrates to cause replication and transcription between artificial base pairs in a complementary manner, nucleic acids containing such artificial base pairs can be amplified and prepared. However, such substrates and base pairs (unnatural nucleotides) are still under development.

Background of Artificial Base Pairs

In natural double-stranded DNA, the "exclusive" A-T and G-C base pairs are formed through specific hydrogen bonding. In recent years, studies have been conducted to develop base pairs that have hydrogen-bonding patterns different from those of natural base pairing and that are capable of eliminating base pairing with natural bases by steric hindrance. For example, Ohtsuki et al. (2001) and Hirao et al. (2002) have designed purine derivatives having a bulky substituent at the 6-position, i.e., 2-amino-6-dimethylaminopurine (x) and 2-amino-6-thienylpurine (s), as well as 2-oxo (1H)pyridine (y) having a hydrogen atom at the site complementary to the bulky substituent, and also have studied x-y and s-y base pairing by the efficiency of Klenow fragment-mediated incorporation into DNA. As a result, the incorporation of y opposite x in the template showed low selectivity, whereas the incorporation of y opposite s showed relatively good selectivity and efficiency (FIG. 1).

The development of the above s-y base pair enabled the selective incorporation of y into RNA. The inventors of the present invention have further conceived that it would be possible to design novel functional molecules such as aptamers and ribozymes once y has been modified to have a functional substituent. Thus, the inventors have developed nucleic acids containing nucleotides, having 5-substituted-2-oxo (1H)pyridin-3-yl bases whose 5-position is substituted with iodine or the like. As to the development history of artificial base pairs, as well as nucleosides and nucleotides having a 5-substituted-2-oxo(1H)pyridin-3-yl group as a base, details can be found in WO2004/007713 (published on Jan. 22, 2004).

Labeling and Detection of Nucleic Acids

Substances such as radioactive elements and fluorescent dyes have previously been used for labeling of nucleic acids. However, nucleic acids containing natural bases have inherent problems; they are labeled only at their ends, or; when any of the labeled natural nucleotides (A, T, G, C) is incorporated, the corresponding bases at a large number of positions are randomly labeled in the inside of their fragments. Thus, it is desired to develop a method for site-specifically labeling the inside of a nucleic acid, e.g., by using a fluorescent dye.

The following documents are listed as reference documents, the entire contents of which are incorporated herein by reference.

Patent Document 1: WO2004/007713

Non-patent Document 1: Battersby, T. R., Ang, D. N., Burgstaller, P., Jurczyk, S. C., Bowser, M. T., Buchanan, D. D., Kennedy, R. T. & Benner, S. A. (1999) Quantitative Analysis of Receptors for Adenosine Nucleotides Obtained via In Vitro Selection from a Library Incorporating a Cationic Nucleotide Analog., J. Am. Chem. Soc., 121, 9781-9789.

Non-patent Document 2: Ellington, A. D. & Szostak, J. W. (1990) In vitro selection of RNA molecules that bind specific ligands., Nature, 346, 818-822.

Non-patent Document 3: Fang, X., Cao, Z., Beck, T. & Tan, W. (2001) Molecular aptamer for real-time oncoprotein platelet-derived growth factor monitoring by fluorescence anisotropy., Anal. Chem., 73, 5752-5757.

Non-patent Document 4: Fujiwara, T., Kimoto, M., Sugiyama, H., Hirao, I. & Yokoyama, S. (2001) Synthesis of 6-(2-Thienyl)purine Nucleoside Derivatives That Form Unnatural Base Pairs with Pyridin-2-one Nucleosides., Bioorg. Med. Chem. Lett., 11, 2221-2223.

Non-patent Document 5: Golden, M. C., Collins, B. D., Willis, M. C. & Koch, T. H. (2000) Diagnostic potential of PhotoSELEX-evolved ssDNA aptamers., J. Biotechnol., 81, 167-178.

Non-patent Document 6: Hirao, I., Madin, K., Endo, Y., Yokoyama, S. & Ellington, A. D. (2000) RNA aptamers That Bind to and Inhibit the Ribosome-inactivating Protein, Pepocin., J. Biol. Chem., 275, 4943-4948.

Non-patent Document 7: Hirao, I., Ohtsuki, T., Fujiwara, T., Mitsui, T., Yokogawa, T., Okuni, T., Nakayama, K., Takio, K., Yabuki, T., Kigawa, T., Kodama, K., Yokogawa, T., Nishikawa, K. & Yokoyama, S. (2002) An unnatural base pair for incorporating amino acid analogs in to proteins., Nat. Biotechnol., 20, 177-182.

Non-patent Document 8: Ishikawa, M., Hirao, I. & Yokoyama, S. (2000) Synthesis of 3-(2-deoxy-β-D-ribofuranosyl)pyridin-2-one and 2-amino-6-(N,N-dimethylamino)-9-(2-deoxy-β-D-ribofuranosyl)purine derivatives for an unnatural base pair., Tetrahedron Lett., 41, 3931-3934.

Non-patent Document 9: Jensen, K. B., Atkinson., B. L., Willis, M. C., Koch, T. D. & Gold, L. (1995) Using in vitro selection to direct the covalent attachment of human immunodeficiency virus type 1 Rev protein to high-affinity RNA ligands., Proc. Natl. Acad. Sci. USA, 92, 12220-12224.

Non-patent Document 10: Jhaveri, S., Rajendran, M. & Ellington, A. D. (2000) In vitro selection of signaling aptamers., Nat. Biotechnol., 18, 1293-1297.

Non-patent Document 11: Latham, J. A., Johnson, R. & Toole, J. J. (1994) The application of a modified nucleotide in aptamer selection: novel thrombin aptamers containing 5-(1-pentynyl)-2'-deoxyuridine., Nucleic Acids Res., 22, 2817-2822.

Non-patent Document 12: Matulic-Adamic, J. & Beigelman, L. (1997) Synthesis of 3-(β-D-Ribofuranosyl)-2-Fluoropyridine and 3-(β-3-D-Ribofuranosyl)-Pyridin-2-one., Tetrahedron Lett., 38, 203-206.

Non-patent Document 13: Meisenheimer, K. M. & Koch, T. H. (1997) Photocross-Linking of Nucleic Acids to Associated Proteins., Crit. Rev. Biochem. Mol. Biol., 32, 101-140.

Non-patent Document 14: Morales, J. C. & Kool, E. T. (1999) Minor Groove Interactions between Polymerase and DNA: More Essential to Replication than Watson-Crick Hydrogen Bonds?, J. Am. Chem. Soc., 121, 2323-2324.

Non-patent Document 15: Ohtsuki, T., Kimoto, M., Ishikawa, M., Mitsui, T., Hirao, I. & Yokoyama, S. (2001) Unnatural base pairs for specific transcription. Proc. Natl. Acad. Sci. USA, 98, 4922-4925.

Non-patent Document 16: Piccirilli, J. A., Krauch, T., Moroney, S. E. & Benner, S. A. (1990) Enzymatic incorporation of a new base pair into DNA and RNA extends the genetic alphabet., Nature, 343, 33-37.

Non-patent Document 17: Piccirilli, J. A., Moroney, S. E. & Benner, S. A. (1991) A C-nucleotide base pair: methylpseudouridine-directed incorporation of formycin triphosphate into RNA catalyzed by T7 RNA polymerase., Biochemistry, 30, 10350-10356.

Non-patent Document 18: Switzer, C. Y., Moreney, S. E. & Benner, S. A. (1993) Enzymatic Recognition of the Base Pair between Isocytidine and Isoguanosine., Biochemistry, 32, 10489-10496.

Non-patent Document 19: Tae, E. L., Wu, Y., Xia, G., Schultz, P. G. & Romesberg, F. E. (2001) Efforts toward Expansion of the Genetic Alphabet: Replication of RNA with Three Base Pairs., J. Am. Chem. Soc., 123, 7439-7440.

Non-patent Document 20: Wu, Y., Ogawa, A. K., Berger, M., McMinn, D. L., Schultz, P. G. & Romesberg, F. E. (2000) Efforts toward Expansion of the Genetic Alphabet: Optimization of Interbase Hydrophobic Interactions., J. Am. Chem. Soc., 122, 7621-7632.

Non-patent Document 21: Yamamoto, R., Baba, T. & Kumar, P. K. (2000) Molecular beacon aptamer fluorescences in the presence of Tat protein of HIV-1., Genes Cells, 5, 389-396.

Non-patent Document 22: Kimoto, M., Endo, M., Mitsui, T., Okuni, T., Hirao, I. & Yokoyama, S. (2004) Site-specific incorporation of a photo-crosslinking component into RNA by T7 transcription mediated by unnatural base pairs., Chem. Biol., 11, 47-55.

Non-patent Document 23: Tuschl, T., Gohlke, C., Jovin, T. M., Westhof, E. & Eckstein, F. (1994) A three-dimensional model for the hammerhead ribozyme based on fluorescence measurements., Science, 266, 785-789.

Non-patent Document 24: Logsdon, N., Lee, C. G. & Harper, J. W. (1992) Selective 5' modification of T7 RNA polymerase transcripts., Anal. Biochem., 205, 36-41.

Non-patent Document 25: Misra, A., Mishra, S. & Misra, K. (2004) Synthesis and fluorescence studies of multiple labeled oligonucleotides containing dansyl fluorophore covalently attached at 2'-terminus of cytidine via carbamate linkage., Bioconjugate Chem., 15, 638-646.

Non-patent Document 26: Gibson, U. E., Heid, C. A. & Williams, P. M. (1996) A novel method for real time quantitative RT-PCR., Genome Res., 6, 995-1001.

Non-patent Document 27: Chehab, F. F. & Kan, Y. W. (1989) Detection of specific DNA sequences by fluorescence amplification: a color complementation assay., Proc. Natl. Acad. Sci. USA, 86, 9178-9182.

Non-patent Document 28: Tyagi, S. & Kramer, F. R. (1996) Molecular beacons: probes that fluoresce upon hybridization., Nat. Biotechnol., 14, 303-308.

Non-patent Document 29: Boguszewska-Chachulska, A. M., Krawczyk, M., Stankiewicz, A., Gozdek, A., Haenni, A. L. & Strokovskaya, L. (2004) Direct fluorometric measurement of hepatitis C virus helicase activity., FEBS Lett., 567, 253-258.

Non-patent Document 30: Bernacchi, S. & Mely, Y. (2001) Exciton interaction in molecular beacons: a sensitive sensor for short range modifications of the nucleic acid structure., Nucleic Acids Res., 29, e62.

Non-patent Document 31: Qin, P. Z. & Pyle, A. M. (1999) Site-specific labeling of RNA with fluorophores and other structural probes., Methods, 18, 60-70.

Non-patent Document 32: Walter, N. G. (2001) Structural dynamics of catalytic RNA highlighted by fluorescence resonance energy transfer., Methods, 25, 19-30.

Non-patent Document 33: Klostermeier, D. & Millar, D. P. (2001) RNA conformation and folding studied with fluorescence resonance energy transfer., Methods, 23, 240-254.

Non-patent Document 34: Watrob, H. M., Pan, C. P. & Barkley, M. D. (2003) Two-step FRET as a structural tool., J. Am. Chem. Soc., 125, 7336-7343.

Non-patent Document 35: Mergny, J. L., Boutorine, A. S., Garestier, T., Belloc, F., Rougee, M., Bulychev, N. V., Koskin, A. A., Bourson, J., Lebedev, A. V., Valeur, B., Thuong, N. T. & Helene, C. (1994) Fluorescence energy transfer as a probe for nucleic acid structures and sequences., Nucleic Acids Res., 22, 920-928.

Non-patent Document 36: Dragon, A. I., Liu, Y., Makeyeva, E. N. & Privalov, P. L. (2004) DNA-binding domain of GCN4 induces bending of both the ATF/CREB and AP-1 binding sites of DNA., Nucleic Acids Res., 32, 5192-5197.

Non-patent Document 37: Jucker, F. M., Phillips, R. M., McCallum, S. A. & Pardi, A. (2003) Role of a heterogeneous free state in the formation of a specific RNA-theophylline complex., Biochemistry, 42, 2560-2567.

Non-patent Document 38: Endo, M., Mitsui, T., Okuni, T., Kimoto, M., Hirao, I. & Yokoyama, S. (2004) Unnatural base pairs mediate the site-specific incorporation of an unnatural hydrophobic component into RNA transcripts., Bioorg. Med. Chem. Lett., 14, 2593-2596.

Non-patent Document 39: Moriyama, K., Kimoto, M., Mitsui, T., Yokoyama, S. & Hirao, I. (2005) Site-specific biotinylation of RNA molecules by transcription using unnatural base pairs., Nucleic Acids Res., 33, e129.

Non-patent Document 40: Kimoto, M., Shirouzu, M., Mizutani, S., Koide, H., Kaziro, Y., Hirao, I. & Yokoyama, S. (2002) Anti-(Raf-1) RNA aptamers that inhibit Ras-induced Raf-1 activation., Eur. J. Biochem., 269, 697-704.

Non-patent Document 41: Jenison, R. D., Gill, S. C., Pardi, A. & Polisky, B. (1994) High-resolution molecular discrimination by RNA., Science, 263, 1425-1429.

Non-patent Document 42: Zimmermann, G. R., Jenison, R. D., Wick, C. L., Simorre, J.-P. & Pardi, A. (1997) Interlocking structural motifs mediate molecular discrimination by a theophylline-binding RNA., Nat. Struct. Biol., 4, 644-649.

Non-patent Document 43: Zimmermann, G. R., Shields, T. P., Jenison, R. D., Wick, C. L. & Pardi, A. (1998) A semiconserved residue inhibits complex formation by stabilizing interactions in the free state of a theophylline-binding RNA., Biochemistry, 37, 9186-9192.

Non-patent Document 44: Zimmermann, G. R., Wick, C. L., Shields, T. P., Jenison, R. D. & Pardi, A. (2000) Molecular interactions and metal binding in the theophylline-binding core of an RNA aptamer., RNA, 6, 659-667.

Non-patent Document 45: Sibille, N., Pardi, A., Simorre, J.-P. & Blackledge, M. (2001) Refinement of local and long-range structural order in theophylline-binding RNA using (13)C-(1)H residual dipolar couplings and restrained molecular dynamics., J. Am. Chem. Soc., 123, 12135-12146.

Non-patent Document 46: Clore, G. M. & Kuszewski, J. (2003) Improving the accuracy of NMR structures of RNA by means of conformational database potentials of mean force as assessed by complete dipolar coupling cross-validation., 125, 1518-1525.

Non-patent Document 47: Stojanovic, M. N. & Kolpashchikov, D. M. (2004) Modular aptameric sensors., J. Am. Chem. Soc., 126, 9266-9270.

Non-patent Document 48: Frauendorf, C. & Jaschke, A. (2001) Detection of small organic analytes by fluorescing molecular switches., Bioorg. Med. Chem., 9, 2521-2524.

Non-patent Document 49: Patel, D. J. & Suri, A. K. (2000) Structure, recognition and discrimination in RNA aptamer complexes with cofactors, amino acids, drugs and aminoglycoside antibiotics., J. Biotechnol., 74, 39-60.

DISCLOSURE OF THE INVENTION

Problems to be Solved by the Invention

The present invention provides a nucleoside or nucleotide having a 5-substituted-2-oxo(1H)pyridin-3-yl group as a base. In one embodiment, the nucleoside or nucleotide of the present invention has a fluorescent dye attached either directly or through a linker to the 5-position of the above base, wherein the fluorescent dye is selected from the group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-(dimethylamino)naphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX), and 6-carboxy-X-rhodamine (6-ROX). 5-FAM and 6-FAM, 5-TAMRA and 6-TAMRA, 5-HEX and 6-HEX, 5-TET and 6-TET, as well as 5-ROX and 6-ROX are collectively expressed herein as FAM, TAMRA, HEX, TET and ROX, respectively, when there is no necessity to distinguish them from each other.

In another embodiment, the nucleoside or nucleotide of the present invention also has a quencher dye attached either directly or through a linker to the 5-position of the above base, wherein the quencher dye is selected from the group consisting of 4-(4-dimethylaminophenylazo)benzoic acid (DAB-CYL), N-methyl-N-[4-[2-methoxy-5-methyl-4-(2-nitro-4-methylphenylazo)phenylazo]phenyl]-4-aminobutyric acid (BHQ1) and N-methyl-N-[4-[2,5-dimethoxy-4-(4-nitrophenylazo)phenylazo]phenyl]-4-aminobutyric acid (BHQ2).

The present invention further provides a nucleic acid incorporating the inventive nucleotide having a 5-substituted-2-oxo(1H)pyridin-3-yl group as a base. Such a nucleotide in the nucleic acid of the present invention can form a base pair with a nucleotide having a 6-substituted 2-aminopurin-9-yl group as a base. In one embodiment of the nucleic acid of the present invention, the above nucleotide having a 5-substituted-2-oxo (1H)pyridin-3-yl group as a base and the above nucleotide having a 6-substituted 2-aminopurin-9-yl group as a base are present in the same single-stranded nucleic acid.

The present invention further provides a method for detecting a target protein. In one embodiment, the detection method of the present invention comprises:

1) synthesizing a nucleic acid incorporating the inventive nucleotide having a 5-substituted-2-oxo(1H)pyridin-3-yl group as a base;

2) allowing the above nucleic acid to bind to a target protein;

3) allowing the target protein to adhere to a support; and 4) measuring the fluorescence of the above nucleic acid bound to the target protein adhered to the support.

In another embodiment, the detection method of the present invention may comprise the following steps instead of the above steps 3) and 4):

3') selectively retaining the target protein in a solution using an ultrafiltration membrane; and 4') measuring the fluorescence of the above nucleic acid bound to the target protein retained in the solution.

The present invention also provides a method for detecting the formation of a nucleic acid duplex by using the nucleotide of the present invention. More specifically, the detection method of the present invention may be accomplished by using Method I or II shown below.

Method I

A method for detecting the formation of a nucleic acid duplex, which comprises:

I-1) inducing hybridization between a nucleic acid containing the inventive nucleotide having, as a base, a 5-substituted-2-oxo(1H)pyridin-3-yl group whose 5-position is substituted with a fluorescent dye and a nucleic acid containing the inventive nucleotide having, as a base, a 5-substituted-2-oxo(1H) pyridin-3-yl group whose 5-position is substituted with a quencher dye; and I-2) measuring a change in the fluorescence spectrum.

Method II

A method for detecting the formation of a nucleic acid duplex, which comprises:

II-1) inducing hybridization between two nucleic acids, each of which contains the inventive nucleotide having, as a base, a 5-substituted-2-oxo(1H)pyridin-3-yl group whose 5-position is substituted with a fluorescent dye, wherein the nucleic acids contain two mutually different fluorescent dyes which allow fluorescence resonance energy transfer (FRET) between them; and II-2) measuring a change in the fluorescence spectrum.

Means for Solving the Problems

As a result of extensive and intensive efforts made to solve the problems stated above, the inventors of the present invention have succeeded in developing an artificial base pair that selectively functions during transcription, and have achieved site-specific introduction of a modified nucleotide into RNA by using this artificial base pair. The modified nucleotide of the present invention is incorporated through transcription into RNA and enables site-specific fluorescent labeling of nucleic acids. The inventors have further succeeded in creating a system for detecting a molecule (nucleic acid, protein) or the like which interacts with a labeled nucleic acid.

Nucleoside or Nucleotide Having a 5-substituted-2-oxo (1H)pyridin-3-yl Group as a Base The present invention provides a nucleoside or nucleotide having a 5-substituted-2-oxo(1H)pyridin-3-yl group as a base. The inventive nucleoside or nucleotide having a 5-substituted pyridine base is characterized by having a fluorescent dye or a quencher dye, which is attached to the 5-position either directly or through a linker.

As used herein, the term "nucleoside" is intended to mean a glycoside compound formed through glycosidic linking between a nucleic acid base and a reducing group of a sugar. It should be noted that the term "nucleic acid base" is intended to encompass adenine, guanine, cytosine, thymine, uracil, and also derivatives thereof. The type of the above "derivative" is not limited in any way. Specific examples include bases equivalent to a 5-substituted-2-oxo(1H)pyridin-3-yl group and bases equivalent to a 2-amino-6-(2-thienyl)purin-9-yl group. The term "nucleotide" refers to a compound in which the sugar moiety of the above nucleoside forms an ester with phosphoric acid, more preferably a mono-, di- or triphosphate ester. The sugar moiety of such a nucleoside or nucleotide may be ribofuranosyl, 2'-deoxyribofuranosyl, or 2'-substituted ribofuranosyl having a substituent (e.g., halogen) at the 2'-position. Likewise, the phosphoric acid moiety may be thiophosphoric acid. Namely, the sugar and phosphoric acid moieties may be in the same form as found in known nucleosides, nucleotides, or derivatives thereof. A ribonucleotide whose sugar moiety is ribofuranosyl can be used as a component of RNA, while a deoxyribonucleotide whose sugar moiety is deoxyribofuranosyl can be used as a component of DNA.

In the nucleoside or nucleotide of the present invention, a fluorescent dye or a quencher dye is attached either directly or through a linker to the 5-position of a base equivalent to a 2-oxo(1H)pyridin-3-yl group.

As a fluorescent dye, any known dye may be used and is preferably selected from the group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-(dimethylamino)naphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX), and 6-carboxy-X-rhodamine (6-ROX). In general, fluorescein and rhodamine are expressed in both open-ring and spiro forms. For example, 5-carboxyfluorescein is as follows when expressed in an open-ring form:

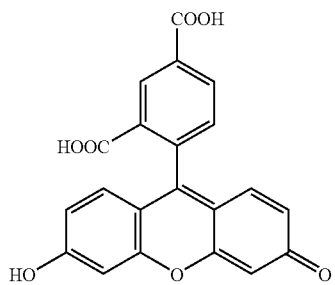

[Formula 1]

and when expressed in a spiro form:

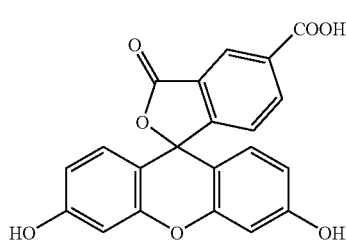

[Formula 2]

Although these fluorescent dyes are expressed in an open-ring form in FIGS. 1 and 3, those expressed in spiro form also fall within the scope of the present invention. These fluorescent dyes are detailed in, e.g., Tuschl et al., 1994; Misra et al., 2004; Gibson et al., 1996 and Chehab et al., 1989.

For example, FAM has an absorption peak wavelength of 493 nm and a fluorescence peak wavelength of 522 nm. Likewise, TAMRA has an absorption peak wavelength of 553 nm and a fluorescence peak wavelength of 578 nm. DANSYL has an absorption peak wavelength of 335 nm and a fluorescence peak wavelength of 518 nm. HEX has an absorption peak wavelength of 535 nm and a fluorescence peak wavelength of 556 nm. TET has an absorption peak wavelength of 521 nm and a fluorescence peak wavelength of 536 nm. 5-ROX has an absorption peak wavelength of 567 nm and a fluorescence peak wavelength of 591 nm. 6-ROX has an absorption peak wavelength of 570 nm and a fluorescence peak wavelength of 590 nm.

Since the nucleotide of the present invention has a fluorescent molecule as a substituent at the 5-position, a nucleic acid containing the nucleotide of the present invention may be detected in a manner dependent on the type of fluorescent molecules. Thus, a nucleic acid containing the inventive nucleotide can be used as a labeled nucleic acid probe to detect substances interacting with the nucleic acid. Moreover, since these individual fluorescent dyes have fluorescent colors different from each other, they can also be used in multiple staining.

As a quencher dye, any known dye may be used and is preferably selected from the group consisting of 4-(4-dimethylaminophenylazo)benzoic acid (DABCYL), N-methyl-N-[4-[2-methoxy-5-methyl-4-(2-nitro-4-methylphenylazo)phenylazo]phenyl]-4-aminobutyric acid (BHQ1) and N-methyl-N-[4-[2,5-dimethoxy-4-(4-nitrophenylazo)phenylazo]phenyl]-4-aminobutyric acid (BHQ2). In the presence of such a quencher dye, energy transfer to the quencher dye inhibits fluorescence emission from a fluorescent dye, thereby resulting in no detection of the fluorescence of the fluorescent dye. More specifically, DABCYL quenches fluorescence emission from fluorescent dyes including FAM, TET, JOE (6-carboxy-4',5'-dichloro-2',7'-dimethoxyfluorescein), HEX, Cy3 (Amersham Biosciences), TAMRA, Cy3.5 (Amersham Biosciences), ROX and Texas Red; BHQ1 quenches fluorescence emission from fluorescent dyes including FAM, Oregon Green 514 (Molecular Probes), TET, Bodipy R6G-X (Molecular Probes), JOE, HEX, Cy3, Rhodamine Red-X (Molecular Probes) and TAMRA; and BHQ2 quenches fluorescence emission from fluorescent dyes including HEX, Cy3, Rhodamine Red-X, TAMRA, Cy3.5, ROX, Texas Red-X, Bodipy TR-X (Molecular Probes), LightCycler 640 (Roche), Boidipy 630/650-X (Molecular Probes) and Cy5 (Amersham Biosciences).

These quencher dyes are detailed in, e.g., Tyagi et al., 1996 and Boguszewska-Chachulska et al., 2004.

When required for convenience sake, the fluorescent dye and/or quencher dye attached either directly or through a linker to the 5-position of the 2-oxo(1H)pyridin-3-yl group is herein also referred to as a "substituent" at the 5-position. The fluorescent dyes and quencher dyes listed above may be purchased from, e.g., Proligo Japan KK, Insitech INC., Invitrogen, Sigma-Aldrich, Biosearch Technologies, Amersham Biosciences, etc.

The fluorescent dye or quencher dye of the present invention may be attached either directly or through a linker to the 5-position of the 2-oxo(1H)pyridin-3-yl group. The type of linker is not limited in any way. For example, the linker is selected from the group consisting of the following chemical formulae I to III.

[Formula 3]

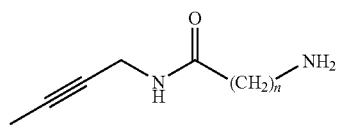

I

[wherein n is selected from integers of 1 to 5]

[Formula 4]

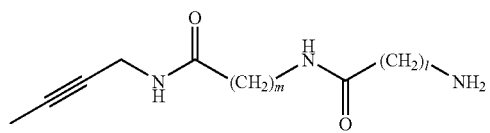

II

[wherein m and l are each independently selected from integers of 1 to 5]

[Formula 5]

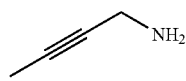

III

The symbols n, m and l shown above are each independently selected and are each preferably 1 to 5, most preferably 5. A short linker causes a slight decrease in incorporation efficiency during transcription reaction. For this reason, a long linker of chemical formula I or II is preferred. Moreover, the aminoalkynyl moiety in chemical formulae I to III may be modified to have a single or double bond instead of its triple bond, i.e., may be replaced by a corresponding aminoalkyl or aminoalkenyl group.

Other linkers available for use include those of diaminoethoxyether type having the following structure:
—NH—(CH$_2$CH$_2$O)$_n$—NH— (see Barnacchi et al., 2001)
or those having the following structure:
—[PO3]-(CH$_2$)$_6$—S—CH$_2$—CO—; or
—[PO3]-(CH$_2$)$_7$—NH— (see Tyagi et al., 1996).

The inventive nucleoside or nucleotide having a 5-substituted-2-oxo(1H)pyridin-3-yl group as a base may be synthesized in any manner. 3-(β-D-Ribofuranosyl)-pyridin-2(1H)-one may first be introduced with a substituent at its 5-position and then with triphosphate. Alternatively, 3-(β-D-ribofuranosyl)-pyridin-2(1H)-one may first be introduced with triphosphate and then with a substituent. In particular, when a large group such as a linker is introduced, a photoreactive group (e.g., iodo) may first be introduced for activation purposes before substitution. Preferably, activation with a reactive group is followed by introduction of a linker, introduction of triphosphate and finally introduction of a substituent. Reaction conditions and others required for substituent introduction can be determined by reference to those of reactions in which these substituents are introduced into pyridine.

As an embodiment of the present invention, FIG. 2 shows synthesis of yTP in which a fluorescent dye or an amino group is introduced at the 5-position through a long linker of chemical formula I. Moreover, FIG. 3 shows synthesis of yTP attached with FAM through a short linker of chemical formula III (short FAM-yTP). The 5-position of the nucleoside y was first iodinated and attached with a linker, followed by triphosphorylation and deprotection to synthesize yTP containing an amino group (NH$_2$-yTP). This NH$_2$-yTP was treated with a succinimide ester of 5-carboxyfluorescein (5-FAM) or 5-carboxytetramethylrhodamine (5-TAMRA) to obtain FAM-yTP and TAMRA-yTP containing these dyes (Examples 1-9).

Alternatively, in the present invention, such a nucleotide having a 2-oxo(1H)pyridin-3-yl group as a base may be modified with a fluorescent dye or a quencher dye not only during synthesis of the nucleotide per se, but also after synthesis of a nucleic acid containing the nucleotide through transcription or the like. In Example 13 described later, the inventors have actually succeeded in introducing a fluorophore into an RNA molecule after synthesis of the RNA molecule by transcription (FIG. 7). It is preferable to use a succinimide ester derivative of a fluorescent molecule in a large excess amount. The nucleotide having a 2-oxo(1H)pyridin-3-yl group as a base, whose 5-position is attached with a linker, is expected to provide higher introduction efficiency when located at the end of a nucleic acid molecule than when located inside (in the middle of) the nucleic acid molecule.

Alternatively, modification with a fluorescent or quencher molecule during synthesis of a nucleotide per se or after synthesis of a nucleic acid by transcription or replication may be accomplished by using an isothiocyanate derivative (e.g., an isothiocyanate derivative of FAM) or a sulfonyl chloride derivative (e.g., DANSYL-chloride) of the fluorescent or quencher molecule, in addition to the above succinimide ester derivative of the fluorescent or quencher molecule.

Nucleic Acid Incorporating the Nucleoside or Nucleotide of the Present Invention The present invention provides a nucleic acid incorporating a nucleotide having a 5-substituted-2-oxo(1H)pyridin-3-yl group as a base. As used herein, the term "nucleic acid" is intended to mean a molecule of a nucleic acid strand in which more than one nucleotide is linked in the direction of 5'→3'.

The nucleic acid of the present invention encompasses single-stranded or double-stranded RNA or DNA. The double-stranded nucleic acid may be DNA/DNA, RNA/RNA, or DNA/RNA. DNA also includes cDNA obtained by reverse transcription using RNA as a template. Alternatively, the nucleic acid may form a triplex, a quadruplex, etc.

With the aim of further expansion of nucleic acid functions, the inventors of the present invention are attempting to design nucleosides or nucleotides having unnatural bases. Embodiments of newly developed artificial base pairs include a base pair between 2-amino-6-(2-thienyl)purine (named "s") and 2-oxo(1H)pyridine (named "y") as well as a base pair between 2-amino-6-(2-thiazolyl)purine (named "v") and y (FIG. 1). In contrast to conventional techniques, if the fluorescent dye (and quencher dye)-labeled fifth base can be introduced by transcription at a specific site in a nucleic acid through artificial base pairing, it significantly facilitates the labeling of nucleic acids and hence the detection of nucleic acids. The present invention achieves these goals by using an artificial base pair, s-y.

The nucleoside or nucleotide of the present invention can form a base pair with a nucleoside or nucleotide having a 6-substituted 2-aminopurin-9-yl group as a base. As shown in FIG. 1 which illustrates y and s (a 2-amino-6-(2-thienyl)purin-9-yl group) or y and v (a 2-amino-6-(2-thiazolyl)purin-9-yl group), the 5-substituted-2-oxo(1H)pyridin-3-yl group of the present invention forms two hydrogen bonds with the 6-substituted 2-aminopurin-9-yl group. The 5-substituted-2-oxo(1H)pyridin-3-yl group of the present invention cannot form any base pair with natural purine bases A (adenine) and G (guanine) in terms of its stereostructure. Likewise, the 6-substituted 2-aminopurin-9-yl group cannot form any base pair with natural T (thymine), U (uracil) and C (cytosine) due to steric hindrance. Thus, the 5-substituted-2-oxo(1H)pyridin-3-yl group of the present invention can specifically form a base pair with the 6-substituted 2-aminopurin-9-yl group.

The nucleic acid of the present invention therefore includes an embodiment wherein a base pair is formed between a nucleotide having a 5-substituted-2-oxo(1H)pyridin-3-yl group as a base and a nucleotide having a 6-substituted 2-aminopurin-9-yl group as a base. The 6-substituted 2-aminopurin-9-yl group is preferably a 2-amino-6-(2-thienyl)purin-9-yl group (s) or a 2-amino-6-(2-thiazolyl)purin-9-yl group (v). As shown in the Example section described later, v is more preferred because the incorporation efficiency of y through transcription is higher in v than in s.

In the present invention, the inventive nucleotide having a 5-substituted-2-oxo(1H)pyridin-3-yl group as a base and a nucleotide having a 6-substituted 2-aminopurin-9-yl group as a base are present in two separate nucleic acid strands and can form a duplex through base pairing. Alternatively, the inventive nucleotide having a 5-substituted-2-oxo(1H)pyridin-3-yl group as a base and a nucleotide having a 6-substituted 2-aminopurin-9-yl group as a base may be present in the same single-stranded nucleic acid. In this case, such a single strand may form a loop structure through base pairing.

As described later, a nucleic acid incorporating the nucleotide of the present invention may be used as antisense DNA or RNA, a ribozyme, an aptamer, or RNA for use in RNAi (RNA interference). Alternatively, DNA or RNA incorporating the nucleotide of the present invention may encode the whole or a part of a protein or peptide.

Synthesis of Nucleic Acid Incorporating the Nucleoside or Nucleotide of the Present Invention The inventive nucleotide having a 5-substituted-2-oxo(1H)pyridin-3-yl group as a base can be incorporated into nucleic acids such as DNA or RNA through transcription, replication or reverse transcription reaction. More specifically, when a nucleic acid containing a nucleotide having a 6-substituted 2-aminopurin-9-yl group as a base, for example, s- or v-containing DNA templates are used to effect transcription reaction with T7 RNA polymerase, the substrate y (yTP) is incorporated into RNA in a site-specific manner, opposite s or v in DNA templates. Since y can be chemically modified at its 5-position, various functional y derivatives can be incorporated into RNA at any specific site.

Thus, without being limited thereto, a nucleic acid incorporating the nucleotide of the present invention may be prepared by a method which comprises specific transcription, replication or reverse transcription by using, as a template, a nucleic acid containing a nucleotide having a 6-substituted 2-aminopurin-9-yl group as a base, whereby the nucleic acid of the present invention is incorporated at a site complementary to the above nucleotide having a 6-substituted 2-aminopurin-9-yl group as a base. Alternatively, the nucleotide of the present invention may be incorporated into DNA or RNA through chemical synthesis, as in the case of nucleosides or nucleotides having natural bases.

For example, in a case where labeled uridine (U) having a fluorescent dye at the 5-position is introduced into RNA through transcription reaction, the transcription reaction must be performed at varying UTP/labeled UTP ratios to randomly replace U positions by labeled U, or alternatively, labeled UTP must be used alone instead of UTP in the transcription reaction to replace all U positions by labeled U. In this case, the introduction of labeled U may cause some change in the higher-order structure of RNA and/or will impair the functions of RNA [Jensen et al., 1995].

In contrast, the 5-substituted-2-oxo(1H)pyridin-3-yl group of the present invention specifically forms a base pair with a 6-substituted 2-aminopurin-9-yl group. This enables the site-selective (site-specific) introduction of a nucleoside or nucleotide having a 5-substituted-2-oxo(1H)pyridin-3-yl group as a base when DNA or RNA having a 6-substituted-2-aminopurin-9-yl group introduced at a desired position is used as a template for transcription, replication or reverse transcription.

These transcription, replication and reverse transcription may be accomplished according to known techniques. Without being limited thereto, for example, it is possible to use T7 RNA polymerase (Takara or other suppliers) for transcription, Klenow fragment (KF) for replication, and AMV Reverse Transcriptase XL (AMV-RT, Life Science) for reverse transcription. In order to avoid removal of a 6-substituted 2-aminopurin-9-yl group during the reaction, the replication may also be accomplished, for example, by using Taq DNA polymerase (Takara Taq™) lacking 3'→5' exonuclease activity to effect PCR amplification of template DNA with an s- or v-containing primer.

A nucleotide having a 6-substituted 2-aminopurin-9-yl group as a base may be synthesized in a known manner, for example, as described in Fujiwara et al., 2001.

In the present invention, the use of specific base pairing between 5-substituted-2-oxo(1H)pyridin-3-yl and 6-substituted 2-aminopurin-9-yl groups enabled the nucleotide of the present invention to be site-selectively (site-specifically) incorporated into RNA via a single step of transcription reaction. If it is possible to freely prepare RNAs composed of 5 different bases including the unnatural base of the present invention, such RNAs allow specific labeling of nucleic acids and hence have great utility and versatility.

Use of the Nucleic Acid of the Present Invention as Antisense DNA or RNA, a Ribozyme or an Aptamer In one embodiment of the present invention, a nucleic acid incorporating the nucleotide of the present invention may be used as antisense DNA or RNA, a ribozyme, an aptamer, or RNA for use in RNAi (RNA interference). The term "antisense DNA or RNA" refers to DNA or RNA capable of inhibiting the expression of a specific gene. It was named to mean that such DNA or RNA is complementary to the full-length or partial sequence of a target gene sequence (sense strand). Antisense DNA or RNA may be used as a tool for artificial regulation of gene expression. Because of the availability of unnatural bases, such antisense DNA or RNA incorporating the nucleotide of the present invention can be designed to have a different complementarity to a target when compared to the case of using natural bases only. The term "ribozyme" is a generic name for catalysts composed of RNA. The term "aptamer" refers to an in vitro-selected nucleic acid having the ability to bind to a specific molecule. The term "RNAi" refers to a system found in cells, which uses a short RNA fragment to regulate translation. It also refers to a technique in which a short RNA fragment corresponding to a target gene is externally incorporated into cells or expressed in cells to thereby prevent the target gene from being expressed.

For example, in vitro-selected aptamers containing a 5-substituted 2-oxo(1H)pyridin-3-yl group enable the creation of RNA molecules having new functions, e.g., the ability to crosslink with a target protein [Kimoto et al, 2004].

There is another report in which a fluorescent molecule is introduced into an RNA aptamer for use as an analyte [Jhaveri et al., 2000; Yamamoto et al., 2000; Fang et al., 2001].

Previous cases reported of in vitro selection employed the following nucleosides as modified bases: fluorescein-12-uracil (F-12-U) [Jhaveri et al., 2000], 5-(1-pentynyl)uracil [Latham et al., 1994], 5-(3"-aminopropynyl)uracil [Battersby et al., 1999], 5-iodouracil (5IU) [Jensen et al., 1995] and 5-bromouracil (5BrU) [Golden., et al., 2000]. In all of these cases, however, replacement between modified base and natural base (T or U) starts at the stage of preparing a DNA or RNA pool.

The inventive nucleic acid (aptamer) containing a fluorescent molecule can be used as an analyte for detecting a target protein. The present invention encompasses a method for detecting a target protein by using the nucleic acid of the present invention. In one embodiment, the detection method of the present invention comprises:

1) synthesizing a nucleic acid incorporating the inventive nucleotide having a 5-substituted-2-oxo(1H)pyridin-3-yl group as a base;

2) allowing the above nucleic acid to bind to a target protein;

3) allowing the target protein to adhere to a support; and 4) measuring the fluorescence of the above nucleic acid bound to the target protein adhered to the support.

In another embodiment, the detection method of the present invention comprises the following steps instead of the above steps 3) and 4):

3') selectively retaining the target protein in a solution using an ultrafiltration membrane; and 4') measuring the fluorescence of the above nucleic acid bound to the target protein retained in the solution.

In the present invention, the target protein to be detected is not particularly limited. Any protein can be readily used as long as a nucleic acid molecule (aptamer) to which the protein binds has been identified for its nucleotide sequence. An example of such a target protein-aptamer combination is Raf-1 protein found in Reference Example 1 of WO2004/007713 (which is incorporated herein by reference) with RNA 9A (FIG. 13 of WO2004/007713) or RNA 9B.

As a support, for example, a nitrocellulose filter or other materials can be used. To these supports, a target protein adheres, but a nucleic acid molecule does not adhere by itself. Only when bound to a protein, a nucleic acid will adhere to the supports via the protein. The protein-nucleic acid complex adhered to the support can be detected by measuring the fluorescence bound to the nucleic acid.

In Example 14 described later, FAM-y was introduced at the 90th position of RNA 9A (having a full-length of 100 nucleotides) which was an RNA aptamer specifically binding to the Raf-1 protein (anti-Raf-1 aptamer). This RNA aptamer carrying the fluorescent dye was mixed with various concentrations of the Raf-1 protein, and this solution was passed through a nitrocellulose filter to adsorb the protein onto nitrocellulose, followed by measuring the fluorescence of the RNA aptamer bound to the protein to thereby determine the protein level, so that the dissociation constant could be calculated (FIG. 8). This is a simple approach that takes the place of conventional RNA labeling techniques using radioisotopes.

The method of the present invention enables quantitative detection of a target protein at a concentration preferably ranging from 0 µmol to 1000 µmol, more preferably from 0 µmol to 500 µmol, and most preferably from 1 µmol to 100 µmol.

Instead of using a support, an ultrafiltration membrane may be used to selectively retain a target protein in a solution. A method for detecting a target protein by using an ultrafiltration membrane may comprise the following steps instead of the above steps 3) and 4):

3') selectively retaining the target protein in a solution using an ultrafiltration membrane; and 4') measuring the fluorescence of the above nucleic acid bound to the target protein retained in the solution. As an ultrafiltration membrane, any known membrane may be used as appropriate for the size of a target protein.

Method for Detecting a Nucleic Acid Duplex

The present invention further provides a method for detecting a nucleic acid duplex by using the nucleic acid of the present invention. More specifically, the detection method of the present invention may be accomplished by using Method I or II shown below.

Method I

A method for detecting the formation of a nucleic acid duplex, which comprises:

I-1) inducing hybridization between a nucleic acid containing the inventive nucleotide having, as a base, a 5-substituted-2-oxo(1H)pyridin-3-yl group whose 5-position is substituted with a fluorescent dye and a nucleic acid containing the inventive nucleotide having, as a base, a 5-substituted-2-oxo(1H)pyridin-3-yl group whose 5-position is substituted with a quencher dye; and I-2) measuring a change in the fluorescence spectrum.

Method II

A method for detecting the formation of a nucleic acid duplex, which comprises:

II-1) inducing hybridization between two nucleic acids, each of which contains the inventive nucleotide having, as a base, a 5-substituted-2-oxo(1H)pyridin-3-yl group whose 5-position is substituted with a fluorescent dye, wherein the nucleic acids contain two mutually different fluorescent dyes which allow fluorescence resonance energy transfer (FRET) between them; and II-2) measuring a change in the fluorescence spectrum.

According to the method of the present invention, when a fluorescent dye and a quencher dye, or alternatively, two different fluorescent dyes are present in the respective two nucleic acid strands, the nucleic acid duplex formation will cause fluorescence resonance energy transfer (FRET) if these dyes are in physical proximity to each other, thus producing a change in the fluorescence spectrum. The method of the present invention detects the formation of a nucleic acid duplex by measuring a FRET-induced change in the fluorescence spectrum.

The term "fluorescence resonance energy transfer (FRET)" refers to a phenomenon in which the excitation energy is transferred by resonance from one fluorescent molecule to another molecule. A molecule providing energy is referred to as a donor, and a molecule receiving the energy is referred to as an acceptor. Once FRET has occurred, a donor losing its energy returns to the ground state, while an acceptor receiving the energy enters an excited state. Thus, the fluorescence of the donor will become weak and, if the acceptor is a fluorescent molecule, its fluorescence will be observed. If the acceptor is a quencher molecule, the fluorescence observed for the donor alone will not be observed as a result of FRET. Standard techniques for FRET-mediated protein detection and nucleic acid detection are known, including a method for detecting a target protein by introducing two FRET-inducing dyes into RNA aptamers (Jhaveri et al., 2000) and a method for detecting a complementary nucleic acid strand with a hairpin structure (Tyagi et al., 1996). For other information on FRET, see Walter et al., 2001 and Klostermeier et al., 2001.

To cause FRET, the following three requirements should be satisfied. i) The donor's fluorescence spectrum and the acceptor's absorption spectrum should overlap with each other. The overlapping area of their spectra is desirably larger, but they do not necessarily have to completely overlap with each other. The donor's fluorescence spectrum and the acceptor's absorption spectrum preferably overlap in 30% or more, more preferably in 50% or more range. ii) The donor and acceptor should be in a closer physical proximity to each other. The distance at which FRET occurs with 50% probability is recognized to be 1 nm to 10 nm, and the efficiency of FRET sensitively varies in response to a change in this distance. For example, in the case of Method I, once the nucleic acids have formed a duplex, the nucleotide having, as a base, a 5-substituted-2-oxo(1H)pyridin-3-yl group (y) substituted with a fluorescent dye is approached by the nucleotide having y substituted with a quencher dye. If the distance between these fluorescent and quencher dyes is preferably 30 nm or less, more preferably 10 nm or less, and most preferably 5 nm or less, it is possible to detect a change in the fluorescence spectrum. iii) The donor and acceptor should be in proper relative orientation to each other.

The maximum absorption spectrum and fluorescence spectrum of the fluorescent dyes used in the present invention are summarized below.

TABLE 1

| | Absorption maxima (nm) | Fluorescence maxima (nm) |
|---|---|---|
| FAM | 493 | 522 |
| TAMRA | 553 | 578 |
| DANSYL | 335 | 518 |
| HEX | 535 | 556 |
| TET | 521 | 536 |
| 5-ROX | 567 | 591 |
| 6-ROX | 570 | 591 |

Thus, embodiments that can be used as an acceptor-donor combination in Method II are as shown below.

TABLE 2

| Donor dye | Acceptor dye |
|---|---|
| FAM | TAMRA, HEX, TET |
| TAMRA | 5-ROX, 6-ROX |
| HEX | TAMRA, 5-ROX, 6-ROX |
| TET | TAMRA, HEX |

On the other hand, in Method I, the quencher dye is not limited by the type of donor and is commonly used as an acceptor.

The method of the present invention is advantageous in allowing site-specific fluorescent labeling of RNA simultaneously with nucleic acid synthesis, e.g., RNA preparation from template DNA. Thus, the method of the present invention can be applied to various detection methods, identification methods, diagnostic methods, etc.

Method for Detecting a Low-Molecular Compound

The present invention further provides a method for detecting a low-molecular compound.

The detection method of the present invention comprises:
1) synthesizing a nucleic acid incorporating the nucleotide of the present invention;
2) contacting the above nucleic acid with a sample likely to contain a low-molecular compound; and
3) measuring a change in the fluorescence spectrum of the above nucleic acid.

In a preferred embodiment of the present invention, the above sample is a solution, and the contacting between the nucleic acid and the sample in step 2) is accomplished in a solution. In the present invention, when the sample is a liquid sample, for example, a solution of a nucleic acid incorporating the nucleotide of the present invention may be introduced into a cell and placed in a spectrofluorometer, to which a liquid sample likely to contain a low-molecular compound may then be added, and used directly for measurement of a change in fluorescence intensity. If there is a change in fluorescence intensity, the target low-molecular compound can be detected and quantified. Quantification may be accomplished, for example, by comparison of the fluorescence spectral data prepared using samples containing the target low-molecular compound at known concentrations with the fluorescence spectrum of the test sample.

Although the low-molecular compound to be measured by the method of the present invention is not limited in any way, it preferably 1) has the ability to bind to a nucleic acid and 2) its binding to a nucleic acid is not affected even if the nucleic acid contains the inventive nucleoside or nucleotide having a 5-substituted-2-oxo(1H)pyridin-3-yl group as a base. Without being limited thereto, such a low-molecular compound has a molecular weight of about 500 to 1000.

In the present invention, such a low-molecular compound is non-limitingly selected from the group consisting of theophylline, a base, a nucleoside or nucleotide, and an amino acid (Non-patent Document 49).

Without being limited thereto, the detection method of the present invention allows detection of a low-molecular compound preferably at about 10 nM to about 10 mM, more preferably at about 100 nM to about 1 mM, and even more preferably at about 1 µM to about 20 µM.

The nucleoside having a 5-substituted-2-oxo(1H)pyridin-3-yl group as a base is herein also referred to as "5-substituted-y" or "5-modified y," and particularly referred to as "fluorescent dye-attached y" when the substituent is a fluorescent dye.

BRIEF DESCRIPTION OF THE DRAWINGS

FIG. 4a shows the absorption spectra of FAM-yTP and TAMRA-yTP, while FIG. 4b shows the fluorescence spectra of FAM-yTP and TAMRA-yTP. The diamonds represent the results obtained for FAM-yTP and the squares represent the results obtained for TAMRA-yTP.

FIG. 5a shows T7 RNA polymerase-mediated introduction of FAM-yTP and TAMRA-yTP into RNA. When N=A in the template was set to 100, the relative yields were 103, 49, 100, 76, 26, 100, 61, 21 and 100 for lanes 1 to 9, respectively.

FIG. 5b shows T7 RNA polymerase-mediated introduction of short FAM-yTP, FAM-yTP, TAMRA-yTP and Dansyl-x-yTP into RNA. When N=A in the template (composed of natural bases only) was set to 100, the relative yields were 72, 108, 80, 96, 62, 110, 48, 94 and 100 for lanes 1 to 9, respectively.

(A) Transcription Scheme for Specific Introduction of y or 5-Modified Bases at the U6 Position Double-stranded template DNA containing s at a site complementary to the introduction site for the 5-modified bases was used in transcription with yTP or 5-substituted yTP (Ph-yTP or I-yTP). Numbering in the theophylline-binding aptamer (41 nucleotides) corresponds to that for the aptamer composed of 33 nucleotides in Non-patent Document 43. Transcription is accomplished on a 20 μl scale and the reaction composition is as follows: 40 mM Tris-HCl buffer (pH 8.0), 24 mM $MgCl_2$, 2 mM spermidine, 5 mM DTT, 0.01% Triton X-100, 1 mM natural nucleotides (NTPs) and 1 mM yTP or 1 mM Ph-yTP or 0.25 mM I-yTP, 2 μCi [α-$^{32}$P]ATP, 2 μM template DNA and 2.5 units/μl of T7 RNA polymerase.

(B) Gel electrophoretic pattern of each aptamer having I-y, y or Ph-y introduced at the U6 position (corresponding to I-y6-41, y6-41 and Ph-y6-41, respectively)

A template containing s (Lanes 1-3: temp59s) or a template containing A instead of s (Lane 4: temp59) was used in transcription with yTP or 5-substituted yTP at the concentration shown above, followed by gel electrophoresis to analyze the resulting products.

(C) Nucleotide Composition Analysis of Transcripts

The transcripts were digested in the presence of 0.75 units $RNaseT_2$ in a 15 mM sodium acetate solution (pH 4.5) at 37° C. for 90 minutes, and the digestion products were two-dimensionally developed on a Merck HPTLC plate (100×100 mm) and analyzed. The developing solvents used for the first and second dimensions were isobutyric acid-ammonia-water (66:1:33 by volume) and isopropyl alcohol-hydrochloric acid-water (70:15:15 by volume), respectively. Spots on the TLC plate (corresponding to individual nucleotides) were quantified for their radioactivity with a bio-imaging analyzer. The results obtained are shown under each TLC panel.

The values were determined by using the following equation.

(Radioactivity of each nucleotide)/(Total radioactivity of all nucleotides)×[(Total number of nucleotides at 5'-neighbor of $A$)=9] [Formula 6]

The theoretical value of each nucleotide is shown in brackets.

Figure 11:
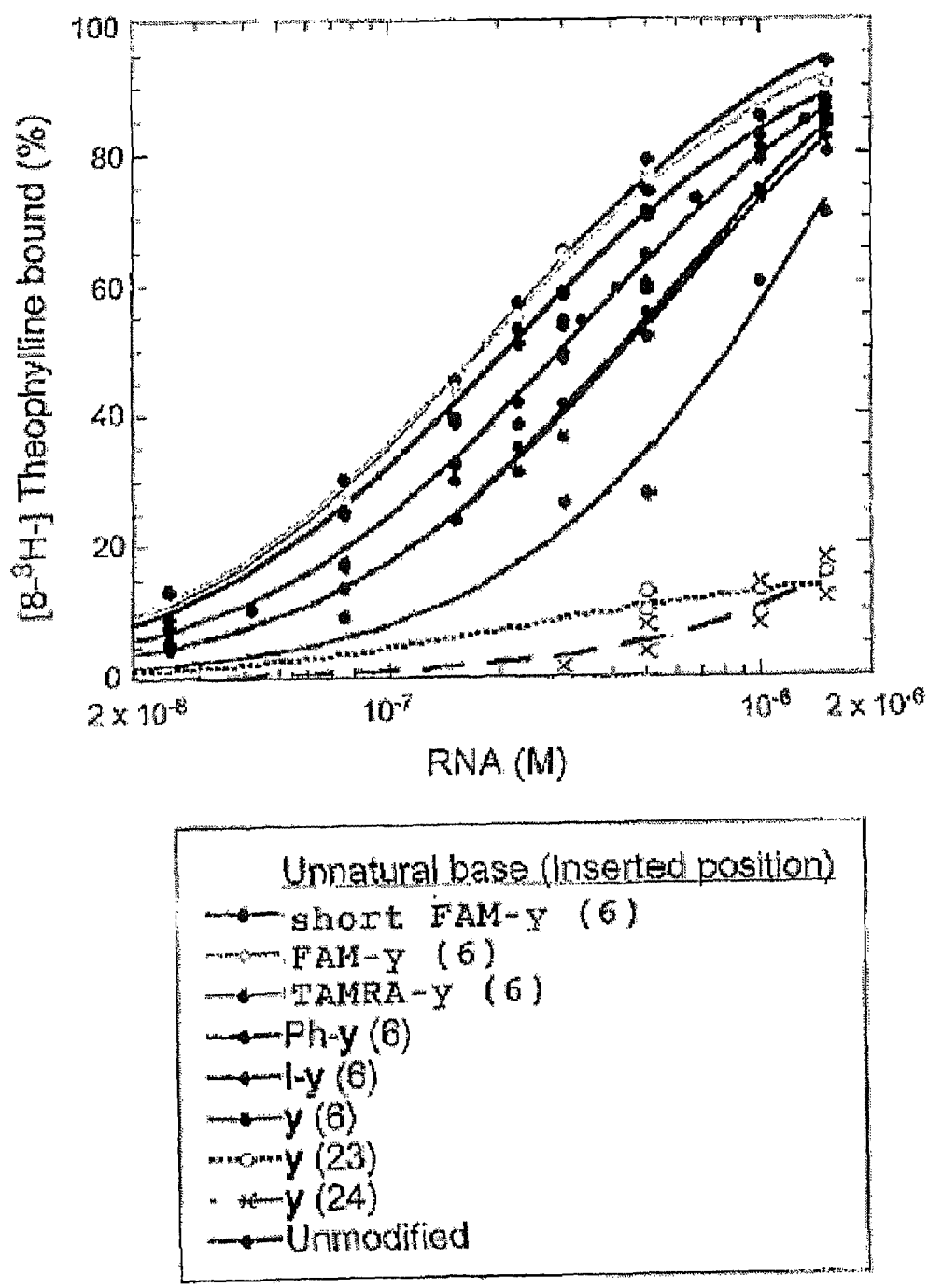
Figure 12:
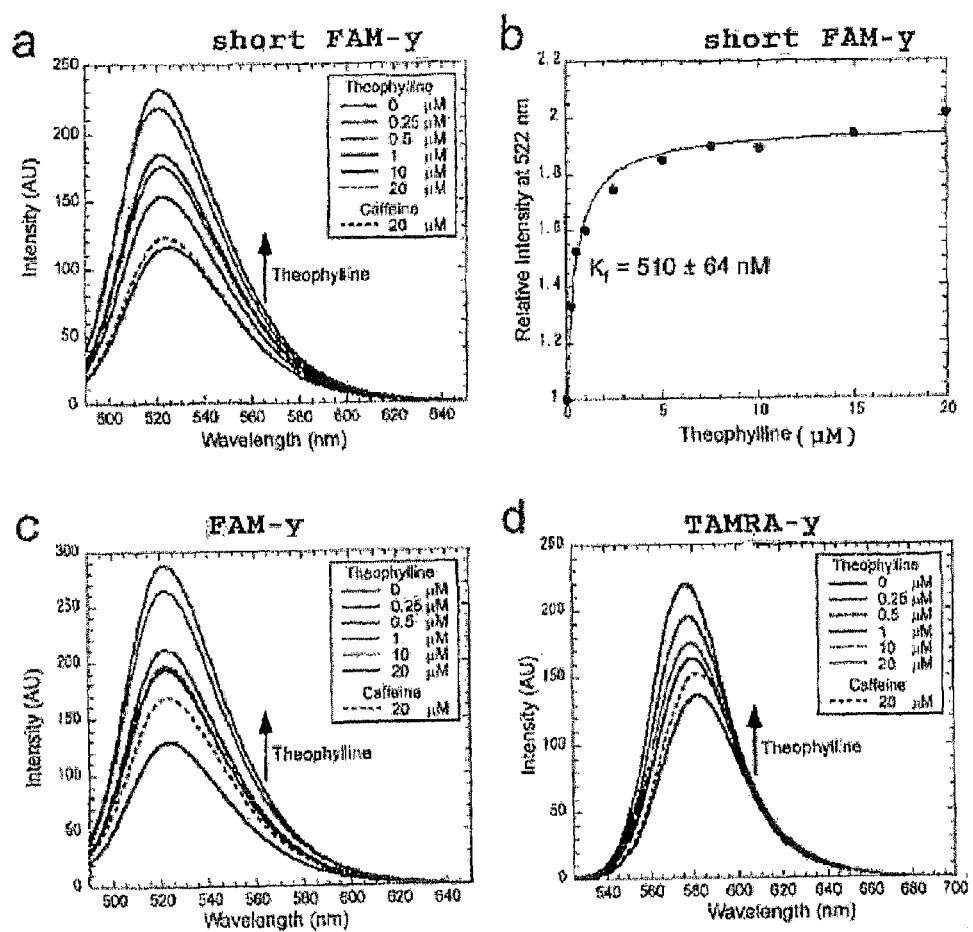

FIG. 11 shows binding curves for RNA aptamers having y or modified-y at a specific position with $^3$H-labeled theophylline. The position at which y or modified-y was introduced is shown in parentheses.
Green line: short FAM-y (6);
Yellow line: FAM-y (6);
Pink line: TAMRA-y (6);
Light-blue line: Ph-y (6);
Light-brown: I-y (6);
Black line: y (6);
Dotted line+open circle: y (23);
Wavy line+cross: y (24);
Orange line: unmodified FIG. 12 shows the fluorescence spectra of theophylline-binding RNA aptamers that are site-specifically labeled with the inventive nucleotides having various unnatural bases.

The RNA aptamers were labeled with any of short FAM-y (a), FAM-y (c) or TAMRA-y (d) and measured for their fluorescence spectra in the presence of theophylline at various concentrations (0-20 μM) or caffeine (20 μM). The black, blue, light-blue, green, orange and red lines represent the results obtained for 0 μM, 0.25 μM, 0.5 μM, 1 μM, 10 μM and 20 μM theophylline, respectively. The red dotted line represents the results obtained for 20 μM caffeine. FIG. 12b is a curve showing theophylline-induced changes in the fluorescence intensity of the short FAM-y-labeled RNA aptamer, wherein the fluorescence intensity at 522 nm is plotted against the theophylline concentration.

EXAMPLES

The present invention will now be further described in the following examples, which are not intended to limit the technical scope of the invention. Based on the detailed description, various changes and modifications will be apparent to those skilled in the art, and such changes and modifications fall within the technical scope of the invention.

The following Examples 1-9 illustrate embodiments of synthesis.

Example 1

Synthesis of 3-(5-O-dimethoxytrityl-β-D-ribofuranosyl)-5-iodo-2-oxo(1H)pyridine 3-(β-D-Ribofuranosyl)-5-iodo-2-oxo(1H)pyridine (178 mg, 505 μmol) was azeotroped three times with anhydrous pyridine in a 10 ml recovery flask and dissolved in anhydrous pyridine (5 ml, 0.1 μM). To this solution, dimethoxytrityl chloride (183 mg, 540 μmol) was added and stirred at room temperature for 1.5 hours. The reaction mixture was poured into ethyl acetate/water and the aqueous layer was removed. The organic layer was washed twice with saturated aqueous sodium bicarbonate, dried over magnesium sulfate and then evaporated to remove the solvent. The resulting crude product was purified by silica gel column chromatography (developing solvent; dichloromethane:methanol=100:0→100:2) to give the desired product as a light-yellow amorphous substance (272 mg, 416 μmol, yield 82%).

$^1$H NMR (270 MHz, DMSO-$d_6$) δ 3.09-3.20 (m, 2H), 3.70-3.86 (m, 8H), 3.92-3.94 (m, 1H), 4.73-4.76 (m, 2H), 5.27 (bs, 1H), 6.89 (d, 2H, J=8.9 Hz), 7.18-7.43 (m, 9H), 7.59-7.61 (m, 2H), 11.9 (bs, 1H).

Example 2

Synthesis of 3-(2,3-di-O-acetyl-5-O-dimethoxytrityl-β-D-ribofuranosyl)-5-iodo-2-oxo(1H)pyridine 3-(5-O-Dimethoxytrityl-β-D-ribofuranosyl)-5-iodo-2-oxo(1H)pyridine synthesized in Example 1 (266 mg, 406 μmol) was azeotroped three times with anhydrous pyridine in a 10 ml recovery flask and dissolved in anhydrous pyridine (4 ml, 0.1 μM). To this solution, acetic anhydride (110 μl, 1.17 mmol) was added and stirred overnight at room temperature. After the reaction mixture was diluted with ethyl acetate, the organic layer was washed with water, saturated aqueous sodium bicarbonate and saturated aqueous sodium chloride, dried over magnesium sulfate and then evaporated to remove the solvent. The resulting oil was dissolved in ethanol (50 ml) and refluxed for 1.5 hours. After concentration, the resulting crude product was purified by silica gel column chromatography (developing solvent; dichloromethane:methanol=100:1→100:4) to give the desired product as a light-yellow amorphous substance (253 mg, 342 μmol, yield 84%).

$^1$H NMR (270 MHz, DMSO-$d_6$) δ 1.96 (s, 3H), 2.04 (s, 3H), 3.14 (dd, 2H, J=6.8 and 12.9 Hz), 3.29-3.31 (m, 1H), 3.73 (s, 6H), 4.10-4.15 (m, 1H), 4.91 (d, 1H, J=3.6 Hz), 5.25-5.33 (m, 2H), 6.88 (d, 4H, J=8.9 Hz), 7.21-7.39 (m, 9H), 7.66 (d, 1H, J=2.3 Hz), 7.74 (d, 1H, J=2.3 Hz).

Example 3

Synthesis of 3-(2,3-di-O-acetyl-5-O-dimethoxytrityl-β-D-ribofuranosyl)-5-[3-(6-trifluoroacetamidohexanamido)-1-propynyl]-2-oxo(1H)pyridine 3-(2,3-Di-O-acetyl-5-O-dimethoxytrityl-β-D-ribofuranosyl)-5-iodo-2-oxo(1H)pyridine synthesized in Example 2 (244 mg, 330 μmol) was azeotroped twice with anhydrous acetonitrile in a 10 ml recovery flask, followed by addition of copper iodide (13.3 mg, 69.8 μmol) and tetrakistriphenylphosphine palladium(0) (36.4 mg, 31.5 μmol). After these materials were dissolved in anhydrous DMF (2 ml), triethylamine (85 μl, 610 μmol) was added while stirring at room temperature and further stirred at room temperature under light-shielding conditions. To this mixture, a solution of N-(2-propynyl)-6-trifluoroacetamidohexanamide (240 mg, 908 μmol) in DMF (1.5 ml) was added dropwise and stirred at room temperature for 3.5 hours. After the reaction mixture was diluted with ethyl acetate/hexane (1:1), the organic layer was washed with water and saturated aqueous sodium chloride, dried over magnesium sulfate and then evaporated to remove the solvent. The resulting crude product was purified by silica gel column chromatography (developing solvent; dichloromethane:methanol=100:0.5→100:3) to give the desired product as a light-yellow amorphous substance (255 mg, 291 μmol, yield 88%).

$^1$H NMR (270 MHz, DMSO-$d_6$) δ 1.16 (m, 2H), 1.41-1.49 (m, 4H), 1.89-2.07 (m, 8H), 3.13 (dd, 2H, J=6.6 and 12.9 Hz), 3.23-3.24 (m, 2H), 3.73 (s, 6H), 3.90-3.92 (m, 2H), 4.10-4.13 (m, 1H), 4.88 (d, 1H, J=3.6 Hz), 5.25-5.33 (m, 2H), 6.87 (d, 4H, J=8.9 Hz), 7.21-7.38 (m, 9H), 7.56-7.58 (m, 2H), 8.13 (t, 1H, J=5.1 Hz), 9.38 (bs, 1H), 12.0 (bs, 1H).

HRMS (FAB, 3-NBA matrix) for $C_{46}H_{49}F_3N_3O_{11}$ [M+1]$^+$: calcd, 876.3319; found, 876.3369.

Example 4

Synthesis of 3-(2,3-di-O-acetyl-β-D-ribofuranosyl)-5-[3-(6-trifluoroacetamidohexanamido)-1-propynyl]-2-oxo(1H)pyridine 3-(2,3-Di-O-acetyl-5-O-dimethoxytrityl-β-D-ribofuranosyl)-5-[3-(6-trifluoroacetamidohexanamido)-1-propynyl]-2-oxo(1H)pyridine synthesized in Example 3 (245 mg, 279 μmol) was dissolved in anhydrous dichloromethane (46 ml). To this solution, dichloroacetic acid (470 μl, 5.69 mmol) was added while stirring at 0° C. and stirred for 15 minutes. The reaction mixture was added dropwise to saturated aqueous sodium bicarbonate at room temperature and stirred vigorously. The aqueous layer was extracted twenty or more times with dichloromethane, and the combined organic layers were dried over magnesium sulfate and then evaporated to remove the solvent. The resulting oil was purified by silica gel column chromatography (developing solvent; dichloromethane:methanol=100:0.5→100:4) to give the desired product as a light-yellow amorphous substance (119 mg, 207 μmol, yield 74%).

$^1$H NMR (270 MHz, DMSO-$d_6$) δ 1.19-1.27 (m, 2H), 1.41-1.55 (m, 4H), 2.00 (s, 3H), 2.02 (s, 3H), 2.08 (t, H J=7.3 Hz), 3.14 (dd, 2H, J=6.8 and 12.9 Hz), 3.49-3.68 (m, 2H), 4.01-4.05 (m, 3H), 4.85 (d, 1H, J=5.3 Hz), 5.15-5.19 (m, 2H), 5.24 (t, 1H, J=5.4 Hz), 7.58 (d, 1H, J=2.5 Hz), 7.66 (d, 1H, J=2.5 Hz), 8.26 (t, 1H, J=5.1 Hz), 9.38 (bs, 1H), 12.1 (bs, 1H).

HRMS (FAB, 3-NBA matrix) for $C_{25}H_{31}F_3N_3O_9$ [M+1]$^+$: calcd, 574.2012; found, 574.2061.

Example 5

Synthesis of 3-(β-D-ribofuranosyl)-5-[3-(6-amino-hexanamido)-1-propynyl]-2-oxo(1H)pyridine 5'-triphosphate (NH$_2$-yTP)

3-(2,3-Di-O-acetyl-β-D-ribofuranosyl)-5-[3-(6-trifluoro-acetamidohexanamido)-1-propynyl]-2-oxo(1H)pyridine synthesized in Example 4 (58.3 mg, 102 μmol) was azeotroped three times with anhydrous pyridine in a 50 ml recovery flask and the reaction vessel was then filled with argon gas. To this, anhydrous pyridine (100 μl) and anhydrous dioxane (300 μl) were added for dissolution purposes, followed by addition of a 1 M dioxane solution of 2-chloro-4H-1,3,2-benzodioxaphosphorin-4-one (110 μl, 110 μmol). After stirring at room temperature for 10 minutes, tri-n-butylamine (100 μl) and a 0.5 M DMF solution of bis(tri-n-butylammonium) pyrophosphate (300 μl) were added and stirred for 10 minutes. A 1% iodine/water/pyridine solution (2 ml) was added and stirred at room temperature for 15 minutes. After addition of a 5% aqueous sodium bisulfite solution (150 μl), the reaction mixture was concentrated under reduced pressure. The resulting oil was mixed with water (10 ml) and stirred at room temperature for 30 minutes, followed by addition of concentrated aqueous ammonia (12 ml). After stirring for 3 hours, this mixture was concentrated under reduced pressure, transferred to a 50 ml tube and then lyophilized. This product was dissolved in concentrated aqueous ammonia, stirred at room temperature for 3 hours and then lyophilized. This product was purified by DEAE Sephadex A-25 column chromatography (1.5×30 cm, linear concentration gradient; 50 mM to 1 M TEAB solution) and C18-HPLC (concentration gradient; 0% to 15% acetonitrile in 0.1 M triethylammonium acetate buffer, pH 7.0) to give the desired product.

$^1$H NMR (270 MHz, D$_2$O) δ 1.13 (t, 18H, J=7.3 Hz), 1.21-1.32 (m, 2H), 1.48-1.61 (m, 4H), 2.19 (t, 2H, J=7.3 Hz), 2.83 (t, 2H, J=7.3 Hz), 3.05 (q, 12H, J=7.3 Hz), 3.95-4.20 (m, 7H), 4.88 (d, 1H, J=3.0 Hz), 7.49 (d, 1H, J=2.0 Hz), 7.83 (d, 1H, J=2.0 Hz).

$^{31}$P NMR (109 MHz, D$_2$O) δ −22.19 (t, 1H, J=20.1 Hz), −10.60 (d, 1H, J=20.1 Hz), −8.84 (d, 1H, J=20.1 Hz).

MS (ESI) for $C_{19}H_{29}N_3O_{15}P_3$ [M−1]$^-$: calcd, 632.08; found, 631.84.

Example 6

Synthesis of 3-(β-D-ribofuranosyl)-5-[3-[6-(fluorescein-5-carboxamido)hexanamido]-1-propynyl]-2-oxo(1H)pyridine 5'-triphosphate (FAM-yTP)

3-(β-D-Ribofuranosyl)-5-[3-(6-aminohexanamido)-1-propynyl]-2-oxo(1H)pyridine 5'-triphosphate synthesized in Example 5 (10 μmol) was transferred to a 5 ml sterilized tube and dissolved in a 0.1 M aqueous sodium bicarbonate solution (pH 8.6, 1.5 ml), followed by addition of a solution of 5-carboxyfluorescein N-hydroxysuccinimide ester (5.5 mg, 11.6 μmol) in DMF (200 μl). The mixture was reacted at room temperature for 3.5 hours with occasional shaking under light-shielding conditions. To this mixture, concentrated aqueous ammonia (1 ml) was added and reacted for 2 hours with occasional shaking. This mixture was concentrated under reduced pressure and lyophilized, followed by DEAE Sephadex A-25 column chromatography (1.5×30 cm, linear concentration gradient; 50 mM to 1 M TEAB solution) and C18-HPLC (concentration gradient; 0% to 50% acetonitrile in 0.1 M triethylammonium acetate buffer, pH 7.0) to give the desired product (3.0 μmol, 30%).

$^1$H NMR (270 MHz, D$_2$O) δ 1.14 (t, 27H, J=7.3 Hz), 1.20-1.40 (m, 2H), 1.45-1.65 (m, 4H), 2.10-2.35 (m, 2H), 2.90-3.60 (m, 22H), 3.70-4.20 (m, 5H), 6.55-6.85 (m, 4H), 7.00-7.40 (m, 4H), 7.50-7.70 (m, 1H), 7.90-8.05 (m, 1H), 8.10-8.20 (m, 1H).

$^{31}$P NMR (109 MHz, D$_2$O) δ −21.75, −10.40, −9.38.

MS (ESI) for $C_{40}H_{39}N_3O_{21}P_3$ [M−1]$^-$: calcd, 990.13; found, 989.98.

Example 7

Synthesis of 3-(β-D-ribofuranosyl)-5-[3-[6-(tetramethylrhodamine-5-carboxamido)hexanamido]-1-propynyl]-2-oxo(1H)pyridine 5'-triphosphate (TAMRA-yTP)

3-(β-D-Ribofuranosyl)-5-[3-(6-aminohexanamido)-1-propynyl]-2-oxo(1H)pyridine 5'-triphosphate synthesized in Example 5 (8 μmol) was transferred to a 5 ml sterilized tube and dissolved in a 0.1 M aqueous sodium bicarbonate solution (pH 8.6, 1.2 ml), followed by addition of a solution of 5-carboxytetramethylrhodamine N-hydroxysuccinimide ester (5 mg, 9.5 μmol) in DMF/water (150/150 μl). The mixture was reacted at room temperature for 3.5 hours with occasional shaking under light-shielding conditions. To this mixture, concentrated aqueous ammonia (1 ml) was added and reacted for 2 hours with occasional shaking. This mixture was concentrated under reduced pressure and lyophilized, followed by DEAE Sephadex A-25 column chromatography (1.5×30 cm, linear concentration gradient; 50 mM to 1 M TEAB solution) and C18-HPLC (concentration gradient; 0% to 50% acetonitrile in 0.1 M triethylammonium acetate buffer, pH 7.0) to give the desired product (4.0 μmol, 50%).

$^1$H NMR (270 MHz, D$_2$O) δ 1.13 (t, 27H, J=7.3 Hz), 1.25-1.40 (m, 2H), 1.50-1.65 (m, 4H), 2.10-2.35 (m, 2H), 3.00-3.22 (m, 32H), 3.40-4.00 (m, 7H), 4.80-4.85 (m, 1H), 6.55-6.60 (m, 1H), 6.65-6.75 (m, 2H), 6.80-6.90 (m, 1H), 6.98-7.05 (m, 1H), 7.05-7.20 (m, 2H), 7.40-7.50 (m, 2H), 7.95-8.05 (m, 1H), 8.08-8.15 (m, 1H).

$^{31}$P NMR (109 MHz, D$_2$O) δ −23.00--22.00 (m, 1H), −11.50--10.50 (m, 1H), −10.50--9.50 (m, 1H).

MS (ESI) for $C_{44}H_{49}N_5O_{19}P_3$ [M−1]$^-$: calcd, 1044.22; found, 1043.90.

Example 8

Synthesis of 3-(β-D-ribofuranosyl)-5-[3-[6-[6-[(5-dimethylaminonaphthalene-1-sulfonyl)amino]hexanamido]hexanamido]-1-propynyl]-2-oxo(1H)pyridine 5'-triphosphate (Dansyl-x-yTP)

3-(β-D-Ribofuranosyl)-5-[3-(6-aminohexanamido)-1-propynyl]-2-oxo(1H)pyridine 5'-triphosphate synthesized in Example 5 (9 μmol) was transferred to a 50 ml sterilized tube and dissolved in a 0.1 M aqueous sodium borate solution (pH 8.5, 1.8 ml), followed by addition of a solution of 6-[(5-dimethylaminonaphthalene-1-sulfonyl)amino]hexanoic acid N-hydroxysuccinimide ester (20 mg, 44 μmol) in DMF (1.8 ml). The mixture was reacted at room temperature for 48 hours with occasional shaking under light-shielding conditions. To this mixture, concentrated aqueous ammonia (1 ml) was added and reacted for 1 hour with occasional shaking. This mixture was concentrated under reduced pressure and then purified by DEAE Sephadex A-25 column chromatography (1.5×30 cm, linear concentration gradient; 50 mM to 1 M TEAB solution) and C18-HPLC (concentration gradient; 0% to 50% acetonitrile in 0.1 M triethylammonium acetate buffer, pH 7.0) to give the desired product (6.2 µmol, 68%).

$^1$H NMR (270 MHz, D$_2$O) δ 0.75-0.90 (m, 2H), 0.92-1.10 (m, 4H), 1.08-1.26 (m, 29H), 1.26-1.40 (m, 2H), 1.40-1.52 (m, 2H), 1.66 (t, 2H, J=7.3 Hz), 2.14 (t, 2H, J=7.3 Hz), 2.72-2.86 (m, 8H), 2.95 (t, 2H, J=6.6 Hz), 3.06 (q, 18H, J=7.3 Hz), 3.85-4.20 (m, 7H), 4.75 (d, 1H, J=3.0 Hz), 7.25-7.32 (m, 2H), 7.52-7.65 (m, 3H), 8.10 (d, 1H, J=7.3 Hz), 8.15 (d, 1H, J=8.9 Hz), 8.33 (d, 1H, J=8.9 Hz).

$^{31}$P NMR (109 MHz, D$_2$O) δ −22.56, −10.54, −10.09. MS (ESI) for C$_{37}$H$_{51}$N$_5$O$_{18}$P$_3$S$_1$ [M−1]$^-$: calcd, 978.22; found, 978.34.

Example 9

Synthesis of 3-(β-D-ribofuranosyl)-5-[3-(fluorescein-5-carboxamido)-1-propynyl]-2-oxo(1H)pyridine 5'-triphosphate (short FAM-yTP)

1) 3-(2,3-Di-O-acetyl-β-D-ribofuranosyl)-5-[3-(2,2-dichloroacetamido)-1-propynyl]-2-oxo(1H)pyridine 3-(2,3-Di-O-acetyl-5-O-dimethoxytrityl-β-D-ribofuranosyl)-5-iodo-2-oxo(1H)pyridine synthesized in Example 2 (268 mg, 362 µmol) was dissolved in CH$_3$CN and evaporated twice in vacuo to dryness. The residue was dissolved in DMF (2 ml), together with Cu(I)I (12.4 mg, 65.2 µmol) and Pd[P(C$_6$H$_5$)$_3$]$_4$ (37.7 mg, 32.6 µmol). After addition of triethylamine (91 µl, 652 µmol), the mixture was stirred in the dark at room temperature. To the mixture, 2,2-dichloro-N-prop-2-ynyl-acetamide (162 mg, 978 µmol) in DMF (1.5 ml) was added dropwise, and the mixture was stirred at room temperature for 3.5 hours. The reaction mixture was diluted with EtOAc. The mixture was washed with H$_2$O and aqueous sodium chloride, dried over MgSO$_4$ and then evaporated in vacuo. The residue was subjected to silica gel column chromatography (0.5-3% CH$_3$OH in CH$_2$Cl$_2$) to purify 3-(2,3-di-O-acetyl-5-O-dimethoxytrityl-β-D-ribofuranosyl)-5-[3-(2,2-dichloroacetamido)-1-propynyl]-2-oxo(1H)pyridine (251 mg, 89%). To 3-(2,3-di-O-acetyl-5-O-dimethoxytrityl-β-D-ribofuranosyl)-5-[3-(2,2-dichloroacetamido)-1-propynyl]-2-oxo(1H)pyridine (251 mg, 323 µmol) in dichloromethane (32 ml), dichloroacetic acid (323 µl, 3.92 mmol) was added and stirred at 0° C. for 15 minutes. The reaction mixture was poured into saturated NaHCO$_3$ solution and stirred vigorously. The aqueous layer was extracted five times with dichloromethane. The combined organic layers were dried over MgSO$_4$ and evaporated in vacuo. The residue was subjected to silica gel column chromatography (2-10% CH$_3$OH in CH$_2$Cl$_2$) to purify the product (136 mg, 88%).

$^1$H NMR (300 MHz, DMSO-d$_6$) δ 2.01 (s, 3H), 2.04 (s, 3H), 3.50-3.70 (m, 2H), 4.00-4.05 (m, 1H), 4.18 (d, 2H, J=5.4 Hz), 4.87 (d, 1H, J=5.6 Hz), 5.10-5.30 (m, 3H), 6.48 (s, 1H), 7.63 (d, 1H, J=2.3 Hz), 7.68 (d, 1H, J=2.0 Hz), 9.10 (t, 1H, J=5.0 Hz), 12.08 (brs, 1H).

HRMS (FAB, 3-NBA matrix) for C$_{19}$H$_{21}$C$_{12}$N$_2$O$_8$ (M+1): calcd, 475.0675; found, 475.0689.

2) 3-(β-D-Ribofuranosyl)-5-[3-(fluorescein-5-carboxamido)-1-propynyl]-2-oxo(1H)pyridine 5'-triphosphate (short FAM-yTP)

3-(2,3-Di-O-acetyl-β-D-ribofuranosyl)-5-[3-(2,2-dichloroacetamido)-1-propynyl]-2-oxo(1H)pyridine (47.5 mg, 100 µmol) was azeotroped three times with anhydrous pyridine in a 50 ml recovery flask and the reaction vessel was then filled with argon gas. To this, anhydrous pyridine (100 µl) and anhydrous dioxane (300 µl) were added for dissolution purposes, followed by addition of a 1 M dioxane solution of 2-chloro-4H-1,3,2-benzodioxaphosphorin-4-one (110 µl, 110 µmol). After stirring at room temperature for 10 minutes, tri-n-butylamine (100 µl) and a 0.5 M DMF solution of bis(tri-n-butylammonium) pyrophosphate (300 µl) were added and stirred for 10 minutes. A 1% iodine/water/pyridine solution (2 ml) was added and stirred at room temperature for 15 minutes. After addition of a 5% aqueous sodium bisulfite solution (150 µl), the reaction mixture was concentrated under reduced pressure. The resulting oil was mixed with water (10 ml) and stirred at room temperature for 30 minutes, followed by addition of concentrated aqueous ammonia (12 ml). After stirring for 3 hours, this mixture was concentrated under reduced pressure, transferred to a 50 ml tube and then lyophilized. This product was dissolved in concentrated aqueous ammonia (3 ml), stirred at 55° C. for 3 hours and then concentrated under reduced pressure. This product was purified by DEAE Sephadex A-25 column chromatography (1.5× 30 cm, linear concentration gradient; 50 mM to 1 M TEAB solution) to give 3-(β-D-ribofuranosyl)-5-[3-amino-1-propynyl]-2-oxo(1H)pyridine 5'-triphosphate. This compound was transferred to a 50 ml sterilized tube and dissolved in a 0.1 M aqueous sodium bicarbonate solution (pH 8.6, 4 ml), followed by addition of a solution of 5-carboxyfluorescein N-hydroxysuccinimide ester (14.5 mg, 30.6 µmol) in DMF (1 ml). The mixture was reacted at room temperature for 12 hours with occasional shaking under light-shielding conditions. To this mixture, concentrated aqueous ammonia (1 ml) was added and reacted for 30 minutes with occasional shaking. This mixture was concentrated under reduced pressure and lyophilized, followed by DEAE Sephadex A-25 column chromatography (1.5×30 cm, linear concentration gradient; 50 mM to 1 M TEAB solution) and C18-HPLC (concentration gradient; 0% to 50% acetonitrile in 0.1 M triethylammonium acetate buffer, pH 7.0) to give the desired product (10.1 µmol, 10%).

$^1$H NMR (270 MHz, D$_2$O) δ 1.14 (t, 32H, J=7.3 Hz), 3.06 (q, 21H, J=7.3 Hz), 4.00-4.35 (m, 7H), 4.80-4.90 (m, 1H), 6.65-6.88 (m, 4H), 6.92-7.06 (m, 2H), 7.25-7.38 (m, 1H), 7.48-7.58 (m, 1H), 7.73-7.85 (m, 1H), 7.95-8.10 (m, 1H), 8.24-8.32 (m, 1H).

$^{31}$P NMR (109 MHz, D$_2$O) δ −22.40, −10.38, −10.38.

MS (ESI) for C$_{34}$H$_{28}$N$_2$O$_{20}$P$_3$ [M−1]$^-$: calcd, 877.04; found, 877.07.

Example 10

Quantum Yield Determination for yTP Derivatives

Figure 1:
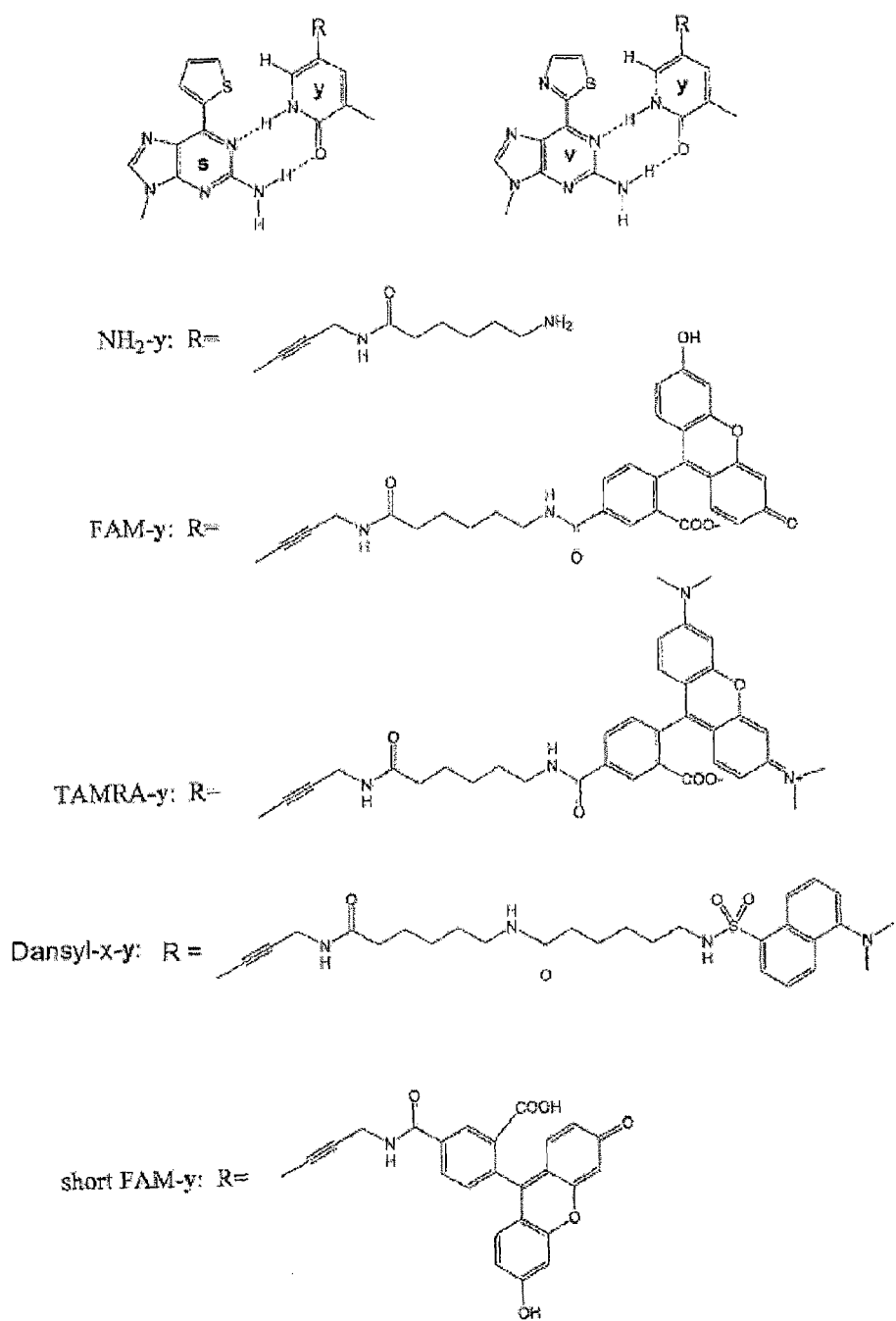
FIG. 1 shows s-y and v-y artificial base pairing, along with y derivatives modified at the 5-position.
Figure 2:
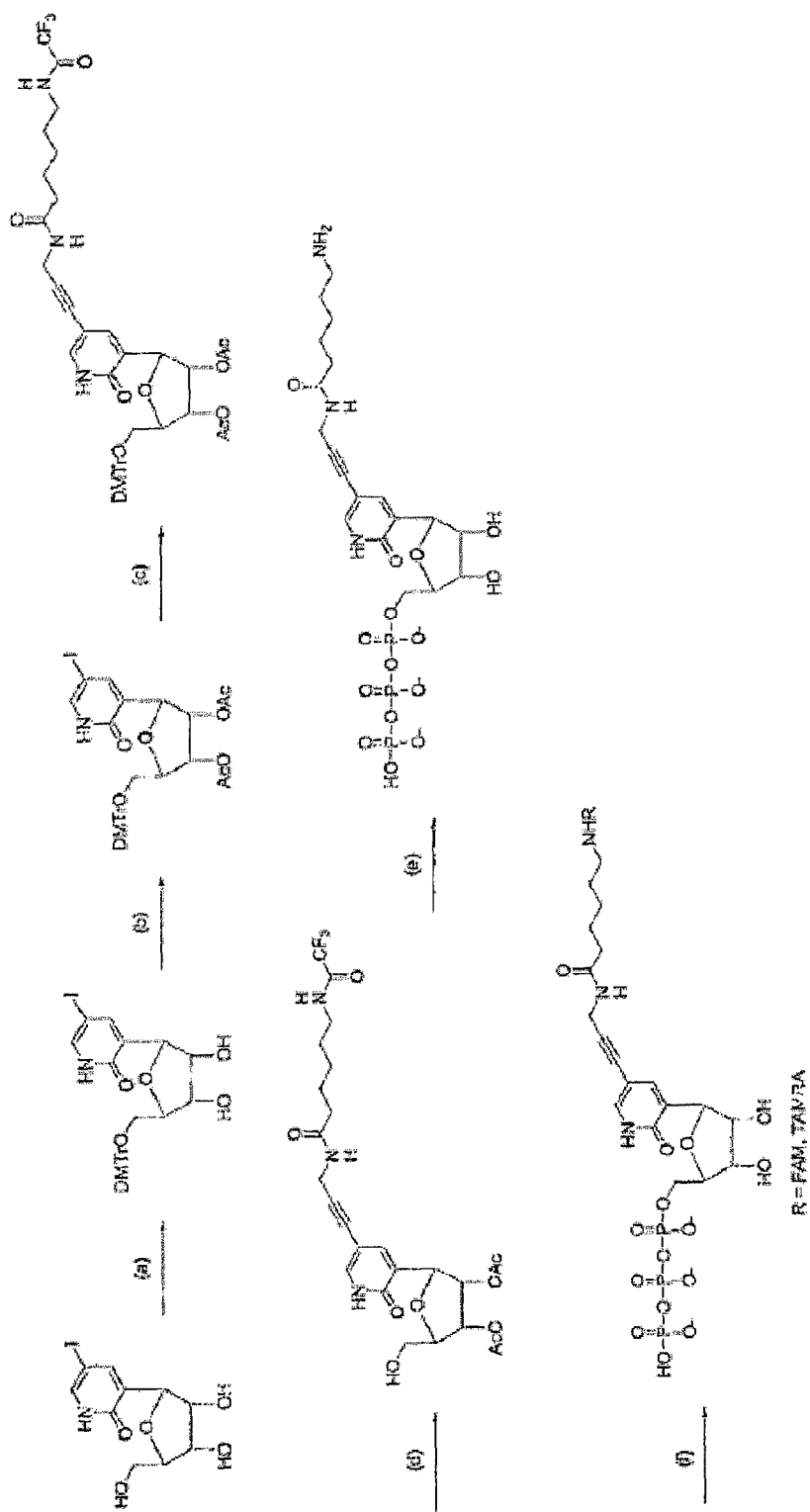
FIG. 2 shows a synthesis scheme for yTP having a fluorescent dye or an amino group attached through a long linker. The conditions and yield in each step are as follows:
(a) DMTr-Cl, pyridine, room temperature, 82%;
(b) i) $(CH_3CO)_2O$, pyridine, room temperature, ii) $C_2H_5OH$, reflux, 84%;
(c) CuI, $Pd[P(C_6H_5)_3]_4$, DMF, $(C_2H_5)_3N$, room temperature, followed by 6-(trifluoroacetamido)caproic acid prop-2-ylamide, 88%;
(d) $CHCl_2COOH$, $CH_2Cl_2$, 0° C., 74%;
(e) 2-chloro-4H-1,3,2-benzodioxaphosphorin-4-one/dioxane, tri-n-butylamine, bis(tri-n-butylammonium)pyrophosphate, $I_2/H_2O$/pyridine, dioxane, room temperature, followed by $NH_4OH$;
(f) R—N-succinimidyl ester/DMF, 0.1 M $NaHCO_3$, aq., room temperature, followed by $NH_4OH$.
Figure 3:
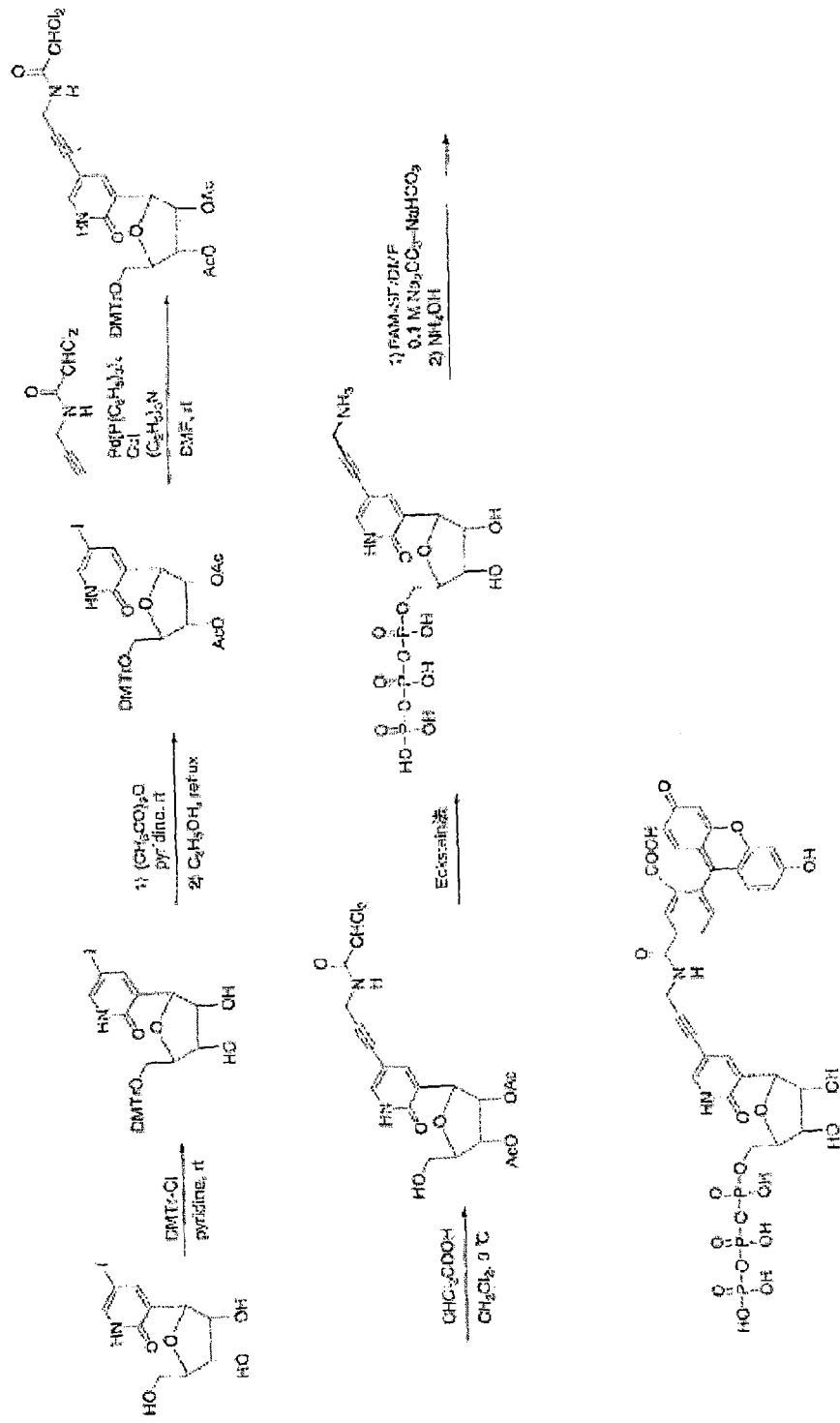
FIG. 3 shows a synthesis scheme for yTP having a fluorescent dye (FAM) attached through a short linker.
Figure 4:
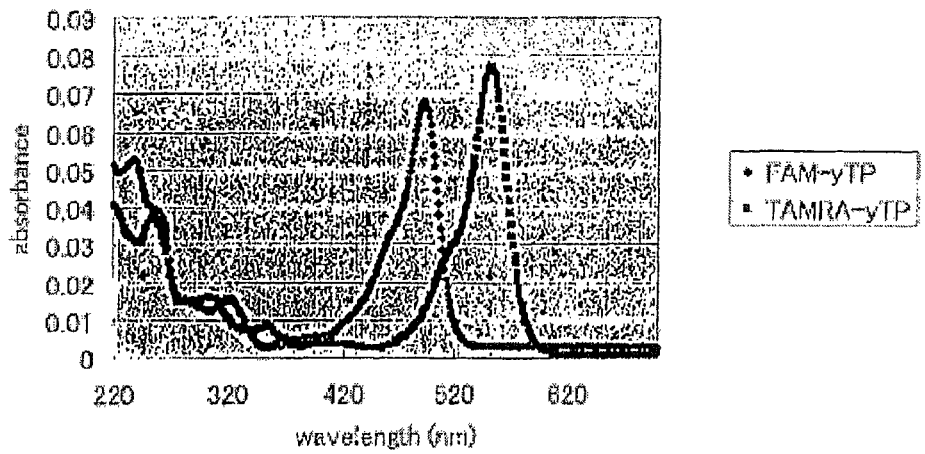
FIG. 4 shows fluorescence properties of FAM-yTP and TAMRA-yTP.
Figure 4:
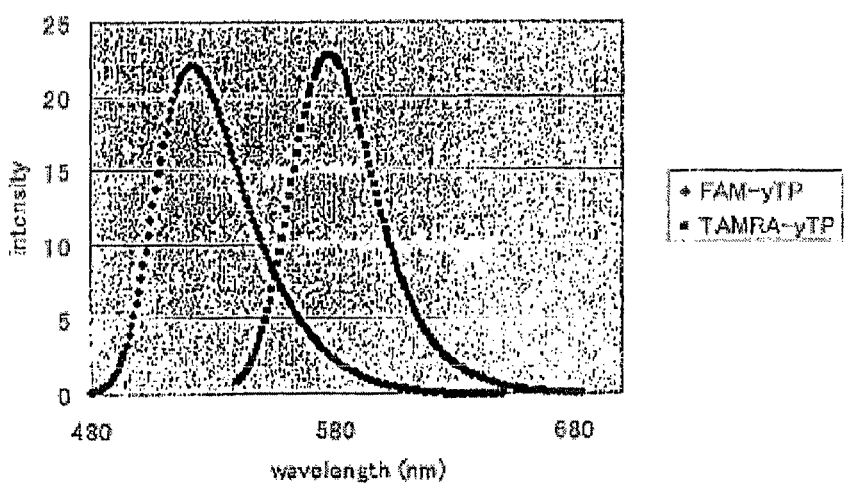

Fluorescence spectra were measured for solutions of FAM-yTP (1.0 µM), TAMRA-yTP (1.0 µM), short FAM-yTP (1.0 µM) and Dansyl-x-yTP (1.0 µM) in 10 mM sodium phosphate buffer (pH 7.0) at 25° C. using a FP-6500 spectrofluorometer (JASCO). A 3×3 mm cell was used for measurement, and the following settings were used to measure each spectrum: response 1.0 s, sensitivity low, and slit width fixed at 3 nm for both excitation and fluorescence sides. The results obtained are shown in FIG. 4.

The quantum yield (φ) was calculated according to the following equation and fluorescein (1.0 µM in 0.1 N NaOH, φs=0.90) was used as a standard.

$$\phi = (F \cdot As \cdot \eta^2 \cdot \phi s)/(A \cdot Fs \cdot \eta_0^2)$$

F: Area of each fluorescence spectrum
A: Absorbance at the excitation wavelength
η: Refractive index (water: 1.33)
s: Standard

TABLE 3

| Compound | Absorption maxima (nm) | Emission maxima (nm) | Quantum yield |
|---|---|---|---|
| FAM-yTP | 493 (ε 62,000) | 522 (excited at 493 nm) | 0.55 |
| TAMRA-yTP | 553 (ε 85,000) | 578 (excited at 553 nm) | 0.50 |
| short FAM-yTP | 493 (ε 70,000) | 521 (excited at 493 nm) | 0.67 |
| Dansyl-x-yTP | 252 (ε 31,400), 319 (ε 10,600) | 387, 541 (excited at 320 nm) | 0.014 |

As shown in FIG. 4 and Table 3, the equilibrium excitation-emission spectrum of FAM-yTP showed a fluorescence spectrum having a maximum at 522 nm when excited at its absorption peak wavelength of 493 nm, and its quantum yield (φ) was 0.55 (in a pH 7.0 aqueous solution). Likewise, the equilibrium excitation-emission spectrum of TAMRA-yTP showed a fluorescence spectrum having a maximum at 578 nm when excited at its absorption peak wavelength of 553 nm, and its quantum yield (φ) was 0.50 (in a pH 7.0 aqueous solution).

The following Examples 11-13 illustrate embodiments of transcription reaction.

Example 11

Transcription Reaction with T7 RNA Polymerase $NH_2$-yTP, FAM-yTP and TAMRA-yTP were each used to analyze transcription reaction with T7 RNA polymerase.

More specifically, double-stranded template DNA (10 μM) was annealed in 10 mM Tris-HCl buffer (pH 7.6) containing 10 mM NaCl under the following conditions: 95° C. for 3 minutes→50° C. for 3 minutes→slow cooling to 4° C. T7 transcription reaction was accomplished in a reaction solution (20 μl) containing 40 mM Tris-HCl buffer (pH 8.0), 24 mM $MgCl_2$, 2 mM spermidine, 5 mM DTT, 0.01% Triton X-100, 2 μCi [γ-$^{32}$P]GTP, 1 mM NTPs, 1 mM modified yTP, 2 μM template DNA, and 50 units of T7 RNA polymerase (Takara).

The template DNA used was a duplex formed between T7 promoter-containing 35-mer template strand and T7 promoter non-template strand 21-mer, which has been modified to have s or v introduced at a single position within the template.

```
T7 promoter-containing 35-mer (SEQ ID NO: 1):
5'-CACTNCTCGGGATTCCCTATAGTGAGTCGTATTAT-3'
``` where N(5)=v (the present invention), s (the present invention) or A (control)

```
T7 promoter non-template strand 21-mer (SEQ ID
NO: 2):
5'-ATAATACGACTCACTATAGGG-3'

Transcript (SEQ ID NO: 3):
5'-GGGAAUCCCGAGN'AGUG-3'
``` where N'(13)=$NH_2$-y, FAM-y or TAMRA-y

The modified substrate was added in the same amount as the natural substrates and reacted at 37° C. for 3 hours, followed by addition of an electrophoresis dye solution (20 μl) containing 10 M urea to stop the reaction. The reaction solution was heated at 75° C. for 3 minutes and then electrophoresed on a 20% polyacrylamide-7 M urea gel. The transcripts were analyzed with a bio-imaging analyzer.

The results obtained are shown in FIG. 5. As shown in FIG. 5, each modified substrate was found to be incorporated into RNA. Based on the fact that the 17-mer RNA fragment shows low mobility in a gel when incorporated with these modified substrates, their incorporation was confirmed. It was further demonstrated that these modified substrates were each efficiently incorporated in a site-specific manner because substantially no band of the native 17-mer was observed in each lane and further because no band with low mobility was observed in the case of using the natural template. Moreover, v provided higher transcription efficiency than s when used as a template base. When compared to transcription reaction using the natural template and substrates only, RNA incorporating $NH_2$-y was obtained in the same yield, while the yield of RNAs incorporating FAM-y and TAMRA-y was 76% and 61%, respectively. These results indicated significantly high efficiency of the incorporation.

Example 12

Nucleotide Composition Analysis for products of T7 RNA polymerase-mediated transcription reaction Subsequent to Example 11, the RNA containing $NH_2$-y was subjected to nucleotide composition analysis.

The same T7 RNA polymerase-mediated transcription reaction as shown in Example 11 was performed in a reaction solution containing 40 mM Tris-HCl buffer (pH 8.0), 24 mM $MgCl_2$, 2 mM spermidine, 5 mM DTT, 0.01% Triton X-100, 2 μCi [α-$^{32}$P]ATP, 1 mM NTPs, 1 mM modified-yTP, 2 μM template DNA, and 50 units of T7 RNA polymerase (Takara). After electrophoresis on a 15% polyacrylamide-7 M urea gel, the transcript was eluted from the gel and collected by ethanol precipitation in the presence of tRNA (0.25 OD).

To this tRNA-containing solution (8.5 μl), RNase $T_2$ (1.5 μl, 1 unit/μl) was added and reacted overnight at 37° C. 0.3 μl of this solution was spotted on a TLC plate (Merck, 10 cm×10 cm) and developed two-dimensionally. As a developing solution, isobutyric acid:concentrated aqueous ammonia:water=66:1:33 (v/v/v) was used for the first dimension and 2-propanol:hydrochloric acid:water=65:10:25 (v/v/v) was used for the second dimension. The developed spots were detected and analyzed with a bio-imaging analyzer.

Figure 6:
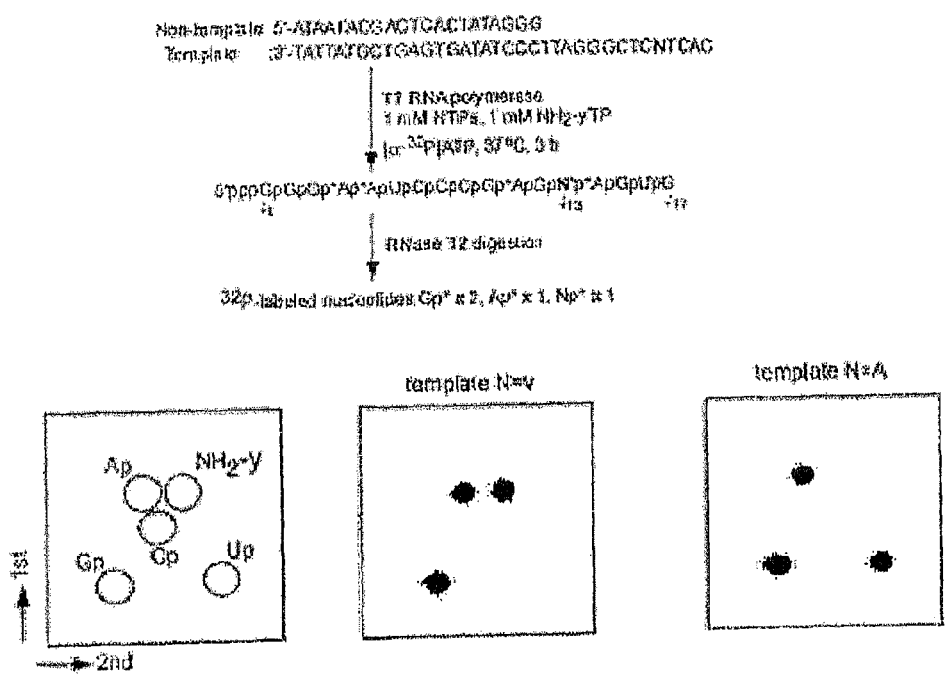
FIG. 6 shows composition analysis of $NH_2$-y and natural nucleotides incorporated into an RNA ligand, as analyzed by two-dimensional TLC.

The results obtained are shown in FIG. 6. In the image from the image analyzer shown in FIG. 6, $^{32}$P-labeled Gp×2, Ap×1 and N'p×1 are detected. In a case where v is present at the N position in the template, $NH_2$-y is detected as the corresponding N' and Up is not observed. On the other hand, in a case where A is present at the N position in the template, Up is detected as the corresponding N' and $NH_2$-y is not observed. The results of nucleotide composition analysis confirmed specific incorporation of $NH_2$-y opposite v.

Example 13

Fluorophore Introduction into RNA 17-mer Containing $NH_2$-y Through Post-Transcriptional Modification The RNA incorporating $NH_2$-y was also subjected to modification with FAM or TAMRA after RNA transcription.

More specifically, the same T7 RNA polymerase-mediated transcription reaction as shown in Example 11 was performed to produce an RNA 17-mer containing NH$_2$-y (SEQ ID NO: 3), which was then purified by electrophoresis (15% polyacrylamide-7 M urea gel), eluted from the gel and collected by ethanol precipitation. The modification reaction was performed at 37° C. for 12 hours on the RNA 17-mer (20 µM, 2.5 µl) in admixture with a succinimide ester of FAM or TAMRA (FAM-SE or TAMRA-SE; 0 mM or 0.2-20 mM in DMSO, 2.5 µl) and 0.1 M sodium tetraborate-HCl buffer (pH 8.3, 15 µl).

An electrophoresis dye solution (20 µl) containing 10 M urea was added to stop the reaction, and the reaction mixture was heated at 75° C. for 3 minutes and electrophoresed on a 20% polyacrylamide-7 M urea gel. The products were then analyzed with a bio-imaging analyzer.

Figure 7:
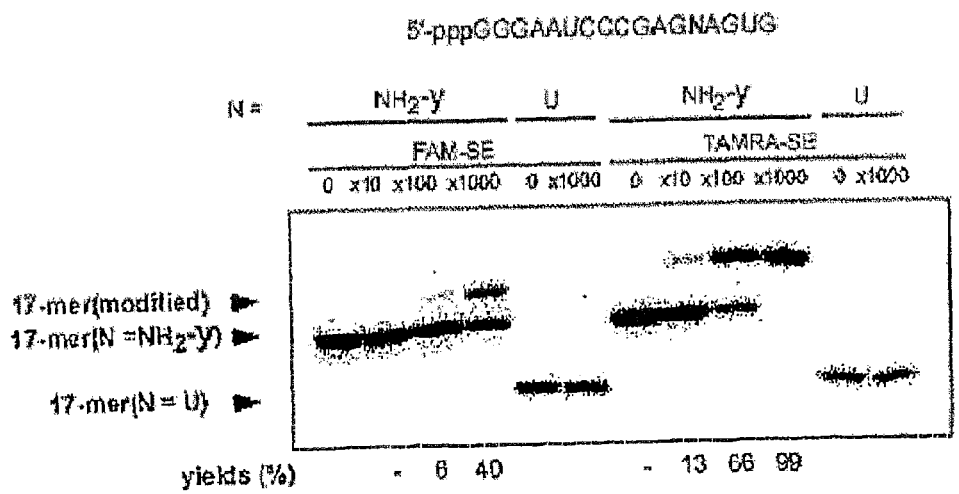
FIG. 7 shows post-transcriptional fluorescent labeling of RNA containing $NH_2$-y. The yields of labeling were 6% and 40% for FAM-SE when used at ×100 and ×1000, respectively, and 13%, 66% and 99% for TAMRA-SE when used at ×10, ×100 and ×1000, respectively.

The results obtained are shown in FIG. 7. As shown in FIG. 7, it was indicated that the use of a large excess amount of each succinimide ester derivative allowed fluorescent labeling of each RNA fragment. In this RNA fragment, NH$_2$-y is located in the middle of the sequence, but it is expected to provide higher modification efficiency when introduced at the end. Moreover, RNA incorporating NH$_2$-y may also be labeled by other various modifications in addition to using fluorescent dyes.

Example 14

Binding Experiment Between Protein and Site-Specifically Fluorescently-Labeled RNA Using Filter-Binding Assay A) Preparation of Template for Transcription Reaction For details of the Raf-1 protein and the RNA aptamer used in this example, see Reference Example 1 of WO2004/007713 which is incorporated herein by reference.

A template for transcription reaction was prepared by the following PCR reaction. The PCR template used was a vector (TOPO 9A) into which the gene of anti-(Raf-1) aptamer 9A (SEQ ID NO: 4) was subcloned, while the enzyme used in the PCR reaction was Taq DNA polymerase lacking 3'→5' exonuclease activity (TaKaRa).

The reaction composition is as follows: 10 mM Tris-HCl buffer (pH 8.3), 50 mM KCl, 1.5 mM MgCl$_2$, 0.2 mM dNTPs, 1 µM primer pair [39.45 (39-mer); 5'-GGTAATACGACTCACTATAGGGAGTGGAGGAATTCATCG (SEQ ID NO: 5), 29.45v90 (29-mer); 5'-GCAGAAGCTTvCTGTCGCTAAGGCATATG (SEQ ID NO: 6)], 1 ng/µl TOPO 9A, and 0.025 units/µl Taq DNA polymerase.

The reaction was accomplished using a PTC-100™ Program Thermal Controller (MJ Research) under the following conditions: [94° C. for 15 seconds, 50° C. for 30 seconds, 72° C. for 1 minute]×15 cycles, and 72° C. for 5 minutes. The reaction solution was passed through Micropure-EZ (Millipore) to remove the enzyme, followed by ethanol precipitation to collect the PCR product. The sample was dissolved in sterilized water and stored for use as a template for T7 transcription reaction.

B) Transcription Reaction with T7 RNA Polymerase (Preparation of RNA 9A Containing FAM-y as the 90th Residue)

T7 transcription reaction was accomplished in a solution containing 40 mM Tris-HCl buffer (pH 8.0), 8 mM MgCl$_2$, 2 mM spermidine, 5 mM DTT, 0.01% Triton X-100, 1 mM natural NTPs, 1 mM FAM-yTP, 25 ng/µl template DNA, and 2.5 U/µl T7 RNA polymerase (TaKaRa). After reaction at 37° C. for 6 hours, an electrophoresis dye solution containing 10 M urea was added in a volume equal to that of the reaction solution to stop the reaction. The reaction solution was heated at 75° C. for 3 minutes and then electrophoresed on a 10% polyacrylamide-7 M urea gel to excise a gel piece containing the desired transcript (9A90F; 100-mer). The desired product was eluted with sterilized water from the gel piece and precipitated with ethanol to collect RNA 9A90F.

C) Binding Experiment Between Protein and RNA Using Filter-Binding Assay

For binding experiment, a GST fusion protein of human Raf-1 RBD (amino acid residues 51-131) was used (Raf-1 protein). In this procedure, the protein-RNA complex was isolated using a nitrocellulose filter based on its ability to adsorb the protein but not the FAM-labeled RNA 9A.

Figure 8:
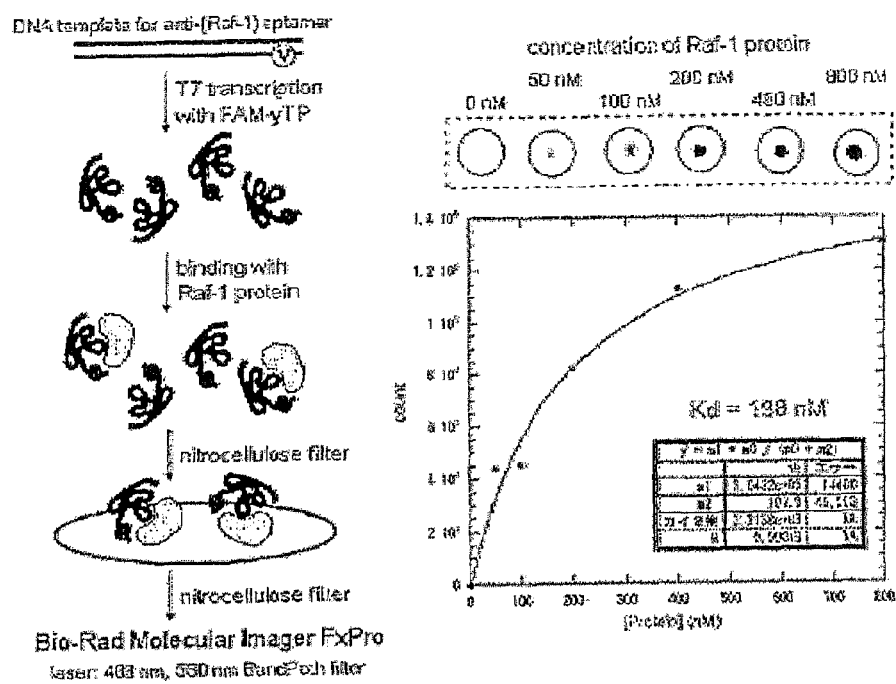
FIG. 8 shows site-specific introduction of FAM-yTP into an anti-(Raf-1) aptamer and an application thereof (Kd measurement). In the final measurement with a Bio-Rad Molecular Imager FxPro, the laser was set to 488 nm and a 530 nm B and Pathfilter was used.

RNA 9A90F (60 µl, final concentration: 10 nM) was mixed with 2 µl Raf-1 protein at various concentrations (final concentration: 50-800 nM) in buffer P (PBS, 5 mM MgCl$_2$) and incubated at room temperature (22° C.) for 30 minutes. 50 µl of the reaction solution was passed through a nitrocellulose filter (Millipore, catalog# HAWP01300) and washed with 200 µl buffer P, followed by measuring the fluorescence level of the RNA adsorbed onto the filter using a fluorescence scanner (Molecular Imager FX Pro, BIO-RAD). The measurement conditions are as follows: filter: 530 nm BP (B and Path); laser wavelength: 488 nm; and PMT setting: 80%. The dissociation constant Kd (corresponding to M$_2$ shown below) was calculated with KaleidaGraph (Albelbeck Software) according to the equation $y = M_0 \times M_1/(M_0+M_2)$ (where y is the measured fluorescence level and M$_0$ is the protein concentration), followed by data fitting using the least squares method. The co-determined M$_0$ corresponds to the fluorescence level of the RNA adsorbed on the filter obtained when RNA-protein binding is saturated (i.e. when the protein level is infinite). The results obtained are shown in FIG. 8.

In this example, as an application of this study, FAM-yTP was introduced at the 90th position of an RNA aptamer specifically binding to the Raf-1 protein (anti-Raf-1 aptamer, having a full-length of 100 nucleotides). This RNA aptamer carrying the fluorescent dye was mixed with various concentrations of the Raf-1 protein, and this solution was passed through a nitrocellulose filter to adsorb the protein onto nitrocellulose, followed by measuring the fluorescence of the RNA aptamer bound to the protein to thereby determine the protein level, so that the dissociation constant could be calculated. This is a simple approach that takes the place of conventional RNA labeling techniques using radioisotopes.

Example 15

Figure 9:
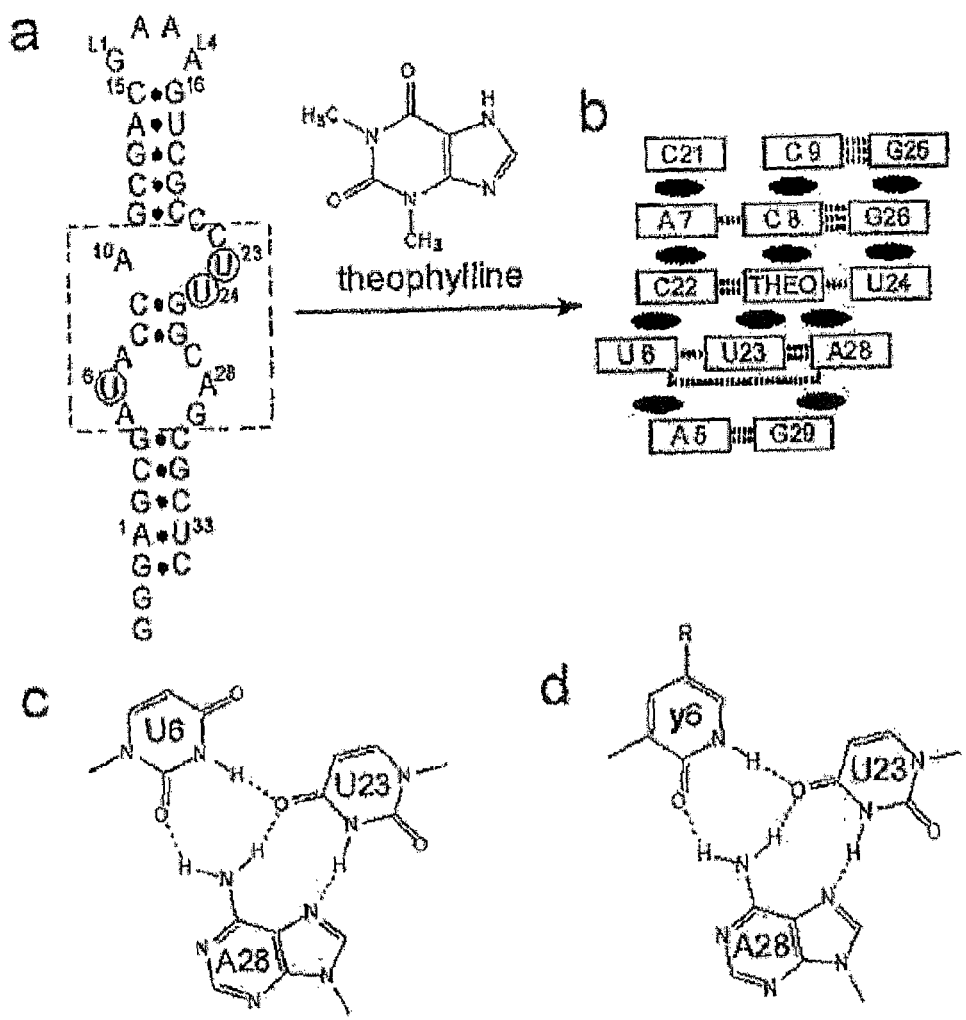
FIG. 9 shows the structure of a theophylline-binding RNA aptamer. (a) Secondary structure; (b) Interaction among nucleotides involved in the theophylline binding site (each dotted line represents a hydrogen bond between bases); (c) Base triplet structure of U6-U23-A28; (d) Triplet structure observed when U6 is replaced with 5-substituted-2-oxo(1H) pyridine.

Introduction of Fluorescent Dye-Attached y into Aptamer Specifically Binding to Theophylline 1) In this example, to study the potential of site-specific fluorescent labeling according to the present invention, fluorescent dye-attached y was introduced into another aptamer specifically binding to the bronchodilator theophylline (Non-patent Documents 37 and 41-46) (FIG. 9*a*). A fluorescent dye located at a specific position in an RNA molecule is useful for detecting a conformational change by measuring a change in fluorescence intensity, or useful for detecting a target molecule.

Theophylline binding causes a unique structural motif to appear in the RNA aptamer (FIG. 9*b*). In the complex, two pairs of triplets, i.e., U6-U23-A28 (FIG. 9*c*) and A7-C8-G26, as well as two independent bases, i.e., C22 and U24 surround theophylline and form a highly specific ligand-binding site. However, this site is not stably formed in the absence of the ligand (Non-patent Documents 37 and 41-46). Non-patent Document 37 reports that a fluorescent adenine analog, 2-aminopurine, was introduced at C27 of the aptamer to analyze the binding mode between the aptamer and theophylline by stopped-flow fluorescence spectroscopy.

The inventors of the present invention have replaced an appropriate site in the aptamer sequence with fluorescent dye-attached y to monitor changes in fluorescence intensity, thereby detecting binding with theophylline. Details are shown below.

Figure 10:
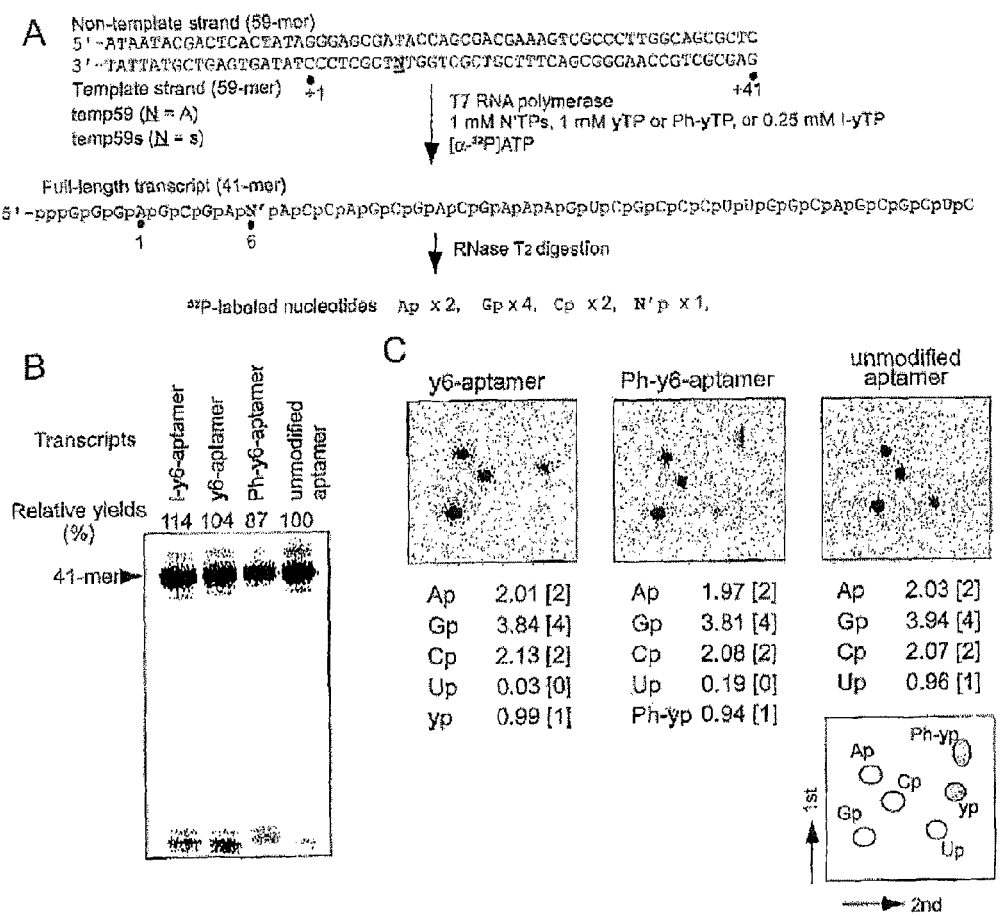
FIG. 10 shows T7 transcription-mediated site-specific introduction of y or 5-substituted y (5-modified bases) into a theophylline-binding aptamer.

2) First, to determine an appropriate site in the theophylline-binding aptamer for the purpose of introducing fluorescent dye-attached y, U6, U23 and U24 in the binding motif of the aptamer were each replaced with unmodified y to study their effect. Each aptamer (41 nucleotides) having y was prepared by T7 transcription using s-containing template DNA in the presence of yTP (FIG. 10a). Site-specific introduction of y into the aptamer was confirmed by nucleotide composition analysis using two-dimensional TLC (FIG. 10c).

The dissociation constant (Kd) for binding of each aptamer to theophylline was measured by the known equilibrium filtration assay (Non-patent Document 41) using $^3$H-labeled theophylline in a solution containing 100 mM HEPES (pH 7.3), 50 mM NaCl and 5 mM MgCl$_2$. The y replacement at U23 and U24 significantly reduced the binding capacity of the aptamers (Kd>1500 nM) when compared to that of the original aptamer (Kd=331±16 nM). As for the replacement of U23, the 4-keto group of U23 forms hydrogen bonds with both U6 and A28 in the base triplet. Since the unnatural base y lacks the 4-keto group of U, the replacement of U23 with y may produce an unfavorable effect on binding. On the other hand, although NMR analysis did not observe a direct interaction between the 4-keto group of U24 and other bases or theophylline, the nitrogen atom at the 3-position of U24 forms a hydrogen bond with theophylline. Thus, the replacement of U24 with y suggests that the 4-keto group of U24 plays an important role in binding motif formation, and that U24 is actually involved in metal binding and U-turn formation in the aptamer structure (Non-patent Documents 42 and 44).

On the other hand, the aptamer in which U6 was replaced with y had a dissociation constant of 217±13 nM and bound to theophylline comparably to the original aptamer. This suggests that removal of the 4-keto group from U6 does not adversely affect the binding capacity of the aptamer. In fact, this 4-keto group is not involved in the U6-U23-A28 base triplet in the aptamer (Non-patent Documents 42 and 43). In addition, when other 5-modified y bases such as 5-phenylethynyl-2-oxo(1H)pyridine (Ph-y) (Non-patent Document 38) and 5-iodo-2-oxo(1H)pyridine (I-y) (Non-patent Document 22) were introduced instead of U6, the resulting aptamers maintained their binding capacity (Kd=536±42 nM for Ph-y replacement and Kd=551±68 nM for I-y replacement, Table 4 and FIG. 11).

Table 4 Theophylline binding capacity of RNA aptamers having modified-y

TABLE 4

| Unnatural base | Inserted positon | $K_d$ [nM]$^a$ | $K_f$[nM]$^b$ |
|---|---|---|---|
| short FAM-y | U6 | 206 ± 16 | 510 ± 64 |
| FAM-y | U6 | 192 ± 11 | 566 ± 115 |
| TAMRA-y | U6 | ~1000 | 488 ± 107 |
| Ph-y | U6 | 536 ± 42 | — |
| I-y | U6 | 551 ± 68 | — |
| y | U6 | 217 ± 13 | — |
| y | U23 | >1500 | — |

TABLE 4-continued

| Unnatural base | Inserted positon | $K_d$ [nM]$^a$ | $K_f$[nM]$^b$ |
|---|---|---|---|
| y | U24 | >1500 | — |
| Unmodified | — | 331 ± 16 | — |

$^a$The dissociation constant for theophylline binding was measured by equilibrium filtration assay using $^3$H-labeled theophylline (20 nM) and various RNA concentrations (25-1500 nM).
$^b$The equilibrium constant for theophylline binding, which was obtained from a change in fluorescence intensity, was determined by fluorescence measurement for 100 nM RNA aptamers having fluorescent dye-attached y at various theophylline concentrations (0-20 µM).

The aptamer in which U6 was replaced with y had a Kd value (Kd=217±13 nM) slightly lower than that of the unmodified aptamer (Kd=331±16 nM). Thus, the replacement of U6 with y allows the formation of a base triplet required to capture theophylline, and U6 is a site suitable for introduction of fluorescent dye-attached y.

3) The inventors of the present invention have prepared aptamers having short FAM-y, FAM-y and TAMRA-y at the U6 position by T7 transcription using s-containing DNA templates, and have examined their binding to theophylline. The Kd value for binding of the aptamer having short FAM-y or FAM-y to $^3$H-labeled theophylline was approximately 200 nM (Table 4), which is the same as that of the unmodified aptamer or the aptamer in which U6 was replaced with y.

The inventors have then measured the fluorescence intensity of the aptamers in the presence or absence of theophylline using a FP-6500 spectrofluorometer. The fluorescence intensity of the aptamer having short FAM-y, FAM-y or TAMRA-y increased depending on the amount of theophylline, and doubled with addition of a saturating concentration of theophylline (5-20 µM) (FIG. 12).

The Kd value for binding of the aptamer having TAMRA-y to $^3$H-labeled theophylline was very high, suggesting that this aptamer would show weak binding to theophylline. However, the fluorescence intensity of the aptamer increased with increasing the theophylline concentration (FIG. 12d). Such a fluorescence intensity change might be caused by conformational rearrangement of the aptamer upon binding to the target substance theophylline. In the absence of theophylline, these fluorescence residues might reside inside the aptamer and stack with the neighboring bases, and thus the stacking would reduce the fluorescence intensity. In the presence of theophylline, once the aptamer has bound to theophylline, the fluorescence residues might move outside and become exposed to the solvent, thereby reducing the base-induced quenching effect and hence increasing the fluorescence intensity.

The equilibrium constant (expressed as "Kf") obtained from a change in the aptamer's fluorescence intensity (FIG. 12 and Table 4) was slightly different from the dissociation constant (Kd) obtained by using $^3$H-labeled theophylline. In the case of the aptamers having short FAM-y and FAM-y, the Kf values were larger than their Kd values. This suggests that when theophylline binds at a concentration around 0.2-0.5 µM, the fluorescent dyes still stack with the neighboring bases inside the structure. In contrast, the Kf value of the aptamer having TAMRA-y was one-half of its Kd value. While not wishing to be bound by theory, this might be because the dimethylamino group of TAMRA causes steric hindrance and facilitates the movement of the TAMRA residue to the outside from the inside of the aptamer structure by weak interaction with theophylline, and also reduces the binding capacity to theophylline. In either case, the Kf values of the aptamers depend on environmental changes of the fluorescence residues induced by a certain concentration of theophylline. Thus, the Kf value is also practically useful for evaluating the detection sensitivity of the aptamer as a sensor.

The fluorescently-labeled aptamers retain their high specificity for theophylline. The fluorescence intensity of the aptamers is not enhanced in the presence of caffeine (20 μM) which is structurally similar to theophylline (FIGS. 12a, c and d). In particular, the aptamer labeled with short FAM-y showed no significant change in its fluorescence intensity, even with addition of 20 μM caffeine (FIG. 12a).

The method of the present invention has much higher sensitivity than conventional modular aptamer sensors and fluorescing molecular switches (Non-patent Documents 47 and 48). In prior art, introduction of another fluorescent dye, 2-aminopurine, at the C27 position of the theophylline-binding aptamer also produced a useful probe (Non-patent Document 37). However, preparation of aptamers having 2-aminopurine requires chemical synthesis. The inventive transcription system using unnatural base pairing is a simple approach for preparing an RNA molecule having a fluorescent probe at a desired position. Moreover, the site-specifically labeled fluorescent dye-attached y bases provided by the present invention allow selective and efficient detection of their target molecules.

In this example, "T7 transcription-mediated site-specific introduction of y or its 5-modified base(s) into theophylline-binding aptamer", "equilibrium filtration assay" and "fluorescence measurement" were accomplished as shown below.

T7 Transcription-Mediated Site-Specific Introduction of y or its 5-Modified Base(s) into Theophylline-Binding Aptamer The chemically synthesized double-stranded template DNA having s was used to introduce y or its modified bases (Ph-y, 1-y and fluorescent dye-attached y) in place of 6U, 23U or 24U.

The sequence of the s-containing template is as shown in FIG. 10A and SEQ ID NO: 7.

In FIG. 10A, numbering in the RNA aptamer (41 nucleotides) (SEQ ID NO: 8) corresponds to that for the aptamer composed of 33 nucleotides in Non-patent Document 43. The template (10 μM of 59 nucleotide coding DNA and 59 nucleotide non-coding DNA) was annealed in a buffer containing 10 mM Tris-HCl (pH 7.6) and 10 mM NaCl by heating at 95° C. and slow cooling to 4° C.

Transcription was accomplished on a 20 μl scale and the reaction composition is as follows: 40 mM Tris-HCl buffer (pH 8.0), 24 mM $MgCl_2$, 2 mM spermidine, 5 mM DTT, 0.01% Triton X-100, 1 mM natural nucleotides (NTPs) and 1 mM yTP or 1 mM Ph-yTP or 0.25 mM I-yTP, 2 μCi [α-$^{32}$P] ATP, 2 μM template DNA and 2.5 units/μl of T7 RNA polymerase (Takara, Kyoto).

After an incubation at 37° C. for 6 hours, an equal volume of a dye solution was added to stop the reaction. The reaction mixture was heated at 75° C. for 3 minutes and then electrophoresed on a gel to purify a transcript of 41 nucleotides.

Equilibrium Filtration Assay

Theophylline binding with an RNA aptamer having y or its 5-modified base at a specific site was analyzed by equilibrium filtration assay (Non-patent Document 41). A solution containing the aptamer at various concentrations (54 μl, 25-1500 nM in 100 mM Hepes (pH 7.3), 50 mM NaCl and 5 mM $MgCl_2$) was mixed with 6 μl of a 200 nM $^3$H-labeled theophylline solution (Moravek), and the mixture was incubated at 25° C. for 5 minutes. The mixture was then placed in a Microcon YM-10 filtration device (Amicon) and concentrated. A 10-μl sample of the filtrate was collected and measured for its radioactivity with a scintillation counter. The fraction of theophylline binding to each RNA aptamer was determined by the difference in the theophylline concentration between the filtrates obtained in the presence and absence of the RNA. The dissociation constant (Kd) for theophylline binding was determined with the program KALEIDAGRAPH using the following equation:

$$y = M_0 \times M_1 / (M_0 + M_2)$$

[where
  y is the fraction of theophylline binding;
  $M_0$ is the RNA concentration;
  $M_1$ is the binding capacity of theophylline; and
  $M_2$ is Kd].

Fluorescence Measurement

The fluorescent profile of each theophylline-binding aptamer having short FMA-y, FAM-y or TAMRA-y in place of U6 was measured at 25° C. in the presence of theophylline (0-20 μM) or caffeine (20 μM) using a FP-6500 spectrofluorometer (JASCO). In fluorescence spectroscopy, a 100 nM concentration of the aptamer was also used, and the excitation wavelength was set to 434 nm (for the aptamer having short FAM-y or FAM-y) or 500 nm (for the aptamer having TAMRA-y) with a 5 nm spectral bandwidth.

The Kf value determined from the equilibrium fluorescence intensity of each modified aptamer was obtained with the program KALEIDAGRAPH using the following equation:

$$y = 1 + C_0 \times C_1 / (C_0 + C_2)$$

[where
  y is the relative fluorescence intensity at 522 nm for FAM and at 578 nm for TAMRA (provided that the fluorescence intensity in the absence of theophylline is set to "1");
  $C_0$ is the theophylline concentration;
  $C_1$ corresponds to the relative increment at the saturating concentration of theophylline; and
  $C_2$ is Kf].

The invention claimed is:

1. A nucleic acid incorporating a nucleotide having a 5-substituted-2-oxo(1H)pyridin-3-yl group as a base, and which has a fluorescent dye attached either directly or through a linker to the 5-position of the base, wherein the fluorescent dye is selected from the group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-(dimethylamino)naphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX), and 6-carboxy-X-rhodamine (6-ROX).

2. A nucleic acid incorporating a nucleotide having a 5-substituted-2-oxo(1H)pyridin-3-yl group as a base, and which has a quencher dye attached either directly or through a linker to the 5-position of the base, wherein the quencher dye is selected from the group consisting of 4-(4-dimethylaminophenylazo)benzoic acid (DABCYL), N-methyl-N-[4-[2-methoxy-5-methyl-4-(2-nitro-4-methylphenylazo)phenylazo]phenyl]-4-aminobutyric acid (BHQ1) and N-methyl-N-[4-[2,5-dimethoxy-4-(4-nitrophenylazo)phenylazo]phenyl]-4-aminobutyric acid (BHQ2).

3. The nucleic acid according to claim 1 or 2, wherein the nucleotide having a 5-substituted-2-oxo(1H)pyridin-3-yl group forms a base pair with a nucleotide having a 6-substituted 2-aminopurin-9-yl group as a base.

4. The nucleic acid according to claim 3, wherein the 6-substituted 2-aminopurin-9-yl group is a 2-amino-6-(2-thienyl)purin-9-yl group or a 2-amino-6-(2-thiazolyl)purin-9-yl group.

5. The nucleic acid according to claim 3, wherein the nucleotide having a 5-substituted-2-oxo(1H)pyridin-3-yl group as a base and the nucleotide having a 6-substituted 2-aminopurin-9-yl group as a base are present in the same single-stranded nucleic acid.

6. The nucleic acid according to claim 3 that has biological activity as antisense DNA, antisense RNA, a ribozyme or an aptamer.

7. The nucleic acid according to claim 4 that has biological activity as antisense DNA, antisense RNA, a ribozyme or an aptamer.

8. The nucleic acid according to claim 5 that has biological activity as antisense DNA, antisense RNA, a ribozyme or an aptamer.

9. A method for detecting a target protein, which comprises:
  1) synthesizing a nucleic acid according to claim 1 or 2;
  2) allowing the nucleic acid to bind to a target protein;
  3) allowing the target protein to adhere to a support; and
  4) measuring the fluorescence of the nucleic acid bound to the target protein adhered to the support.

10. A method for detecting a target protein, which comprises:
  a) synthesizing a nucleic acid according to claim 1 or 2;
  b) allowing the nucleic acid to bind to a target protein;
  c) selectively retaining the target protein in a solution using an ultrafiltration membrane; and
  d) measuring the fluorescence of the nucleic acid bound to the target protein retained in the solution.

11. A method for detecting the formation of a nucleic acid duplex, which comprises:
  i) inducing hybridization between a nucleic acid incorporating a nucleotide having a 5-substituted-2-oxo(1H)pyridin-3-yl group as a base, and which has a fluorescent dye attached either directly or through a linker to the 5-position of the base, wherein the fluorescent dye is selected from the group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-(dimethylamino)naphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX), and 6-carboxy-X-rhodamine (6-ROX), and a nucleic acid incorporating a nucleotide having a 5-substituted-2-oxo(1H)pyridin-3-yl group as a base, and which has a quencher dye attached either directly or through a linker to the 5-position of the base, wherein the quencher dye is selected from the group consisting of 4-(4-dimethylaminophenylazo)benzoic acid (DABCYL), N-methyl-N-[4-[2-methoxy-5-methyl-4-(2-nitro-4-methylphenylazo)phenylazo]phenyl]-4-aminobutyric acid (BHQ1) and N-methyl-N-[4-[2,5-dimethoxy-4-(4-nitrophenylazo)phenylazo]phenyl]-4-aminobutyric acid (BHQ2); and ii) measuring a change in the fluorescence spectrum.

12. A method for detecting the formation of a nucleic acid duplex, which comprises:

I) inducing hybridization between two nucleic acids according to claim 1, wherein the nucleic acids contain two mutually different fluorescent dyes which allow fluorescence resonance energy transfer (FRET) between them; and II) measuring a change in the fluorescence spectrum.

13. A method for detecting a low-molecular weight compound, which comprises:

A) synthesizing a nucleic acid according to claim 1 or 2;

B) contacting the nucleic acid with a sample likely to contain a low-molecular weight compound; and C) measuring a change in the fluorescence spectrum of the nucleic acid.

14. The method according to claim 13, wherein the sample is a solution and the contacting between the nucleic acid and the sample in step B) is accomplished in a solution.

15. The method according to claim 13, wherein the low-molecular weight compound is selected from the group consisting of theophylline, a base, a nucleoside or nucleotide, and an amino acid.

* * * * *